United States Patent [19]

Tripp et al.

[11] Patent Number: 5,750,391
[45] Date of Patent: May 12, 1998

[54] FILARIID NEMATODE CYSTEINE PROTEASE PROTEINS

[75] Inventors: Cynthia Ann Tripp; Glenn R. Frank, both of Ft. Collins; Robert B. Grieve, Windsor, all of Colo.

[73] Assignee: Heska Corporation, Ft. Collins, Colo.

[21] Appl. No.: 463,989

[22] Filed: Jun. 5, 1995

Related U.S. Application Data

[63] Continuation of Ser. No. 249,552, May 26, 1994, abandoned.

[51] Int. Cl.$^6$ .................................. C12N 9/48; C12N 9/50
[52] U.S. Cl. ........................................ 435/212; 435/219
[58] Field of Search ....................... 424/94.65; 435/212, 435/219

[56] References Cited

U.S. PATENT DOCUMENTS

| | | | |
|---|---|---|---|
| 4,657,850 | 4/1987 | Grieve | 435/7 |
| 4,788,149 | 11/1988 | Cerami et al. | 435/212 |

FOREIGN PATENT DOCUMENTS

| | | |
|---|---|---|
| 0 524 834 A2 | 1/1993 | European Pat. Off. . |
| WO 93/10225 | 5/1993 | WIPO . |
| 94/06280 | 3/1994 | WIPO . |
| WO 94/09142 | 4/1994 | WIPO . |

OTHER PUBLICATIONS

Maki, J. et al. (Mar. 1986) "Demonstration of carboxyl and thiol protease activities in adult *Schistosoma mansoni, Dirofilaria immitis, Angiostrongylus cantonensis* and *Ascaris suum*" J. Helminthol. 60(1):31–37.

Sreedhara Swamy, K.H. et al. (Sep. 1983) "Isolation, partial purification and some properties of two acid proteases from adult *Dirofilaria immitis*" Mol. Biochem. Parasit. 9:1–14.

Richer, J.K. et al. (1992) "*Dirofilaria immitis*: proteases produced by third–and fourth–stage larvae" *Exp. Parasitology* 75(2):213–222.

Richer, J.K. (1992) "Proteases produced by *Dirofilaria immitis* third–and fourth–stage larvae" *Diss. Abstr. Int'l.* 53(6B):2599.

Cox et al., "Molecular Cloning and Primary Sequence of a Cysteine Protease Expressed by *Haemonchus contortus* Adult Worms", pp. 25–34, 1990, *Mol. Biochem. Parasitol.,* vol. 41.

Dumermuth et al., "The Astacin Family of Metalloendopeptidases", pp. 21381–21385, 1991, *J. Biol. Chem.,* vol. 266, No. 32.

Eakin et al., "Amplification and Sequencing of Genomic DNA Fragments Encoding Cysteine Proteases from Protozoan Parasites", pp. 1–8, 1990, *Mol. Biochem. Parasitol.,* vol. 39.

Gomis–Rüth et al., Refined 1.8 Å X–Ray Crystal Structure of Astacin, a Zinc–Endopeptidase from the Crayfish *Astacus astacus* L., pp. 945–968, 1993, *J. Mol. Biol.,* vol. 229.

Heussler et al., "Cloning of a Protese Gene Family of *Fasciola hepatica* by the Polymerase Chain Reaction", pp. 11–23, 1994, *Mol. Biochem. Parasitol.,* vol. 64.

Jiang et al., "Families of Metalloendopeptidases and Their Relationships", pp. 110–114, 1992, *FEBS Letters,* vol. 312, No. 2,3.

North et al., "Cysteine Proteinases of Parasitic Protozoa" pp. 270–275, 1990, *Parasitol. Today,* vol. 6, No. 8.

Pratt et al., "Cloning and Sequence Comparisons of Four Distinct Cysteine Proteases Expressed by *Haemonchus contortus* Adult Worms", pp. 209–218, 1992, *Mol. Biochem. Parasitol.,* vol. 51.

Ray et al., "Gut–Specific and Developmental Expression of *Caenorhabditis elegans* Cysteine Protease Gene", pp. 239–250, 1992, *Mol. Biochem. Parasitol.,* vol. 51.

Richer et al., "*Dirofilaria immitis*: Effect of Fluoromethyl Ketone Cysteine Protease Inhibitors on the Third–to Fourth–Stage Molt", pp. 1–11, 1993, *Exp. Parasitol.,* vol. 76.

Richer et al., "*Dirofilaria immitis*: Proteases Produced by Third–and Fourth–Stage Larvae", pp. 213–222, 1992, *Exp. Parasitol.,* vol. 75.

Sakanari et al., "Serine Proteases from Nematode and Protozoan Parasites: Isolation of Sequence Homologs Using Generic Molecular Probes", pp. 4863–4867, 1989, *Proc. Natl. Acad. Sci. USA,* vol. 86.

Swamy et al., "Isolation, Partial Purification and Some Properties of Two Acid Proteases from Adult *Dirofilaria immitis*", pp. 1–14, 1983, *Mol. Biochem. Parasitol.,* vol. 9.

Wilson, et al., "2.2 Mb of Contiguous Nucleotide Sequence from Chromosome III of *C. elegans*" pp. 32–38, 1994, *Nature,* vol. 368, Mar.

Authie, E., 1994, "Trypanosomiasis and Trypanotolerance in Cattle: A Role for Congopain?", *Parasitology Today,* 10(9):360–364.

Britton, et al., 1995, "The Secreted and Somatic Proteinases of the Bovine Lungworm *Dictyocaulus viviparus* and their Inhibition by Antibody from Infected and Vaccinated Animals", *Parasitology,* 46:119–122.

Cichutek, K., 1994, "Nucleic Acid Immunization: a prophylactic gene therapy?" *Vaccine,* 12(16):1520–1525.

Donnelly, et al., 1994, "Immunization with DNA", *Immunological Methods,* 176:145–152.

(List continued on next page.)

*Primary Examiner*—Robert A. Wax
*Assistant Examiner*—Kawai Lau
*Attorney, Agent, or Firm*—Sheridan Ross P.C.

[57] ABSTRACT

The present invention relates to parasite astacin metalloendopeptidase and filariid cysteine protease proteins, nucleic acid molecules having sequences that encode such proteins, antibodies raised against such proteins and compounds that can inhibit the activities of parasite astacin metalloendopeptidases or cysteine proteases. The present invention also includes methods to obtain such nucleic acid molecules, proteins, antibodies and inhibitors. The present invention also includes therapeutic compositions comprising such nucleic acid molecules, proteins, antibodies and inhibitors as well as their use to protect animals from disease caused by parasites, such as heartworm.

9 Claims, No Drawings

OTHER PUBLICATIONS

Harrop, et al., 1995, "Amplification and characterization of cysteine proteinase genes from nematodes", *Trop. Med. Parasitol.*, 46:119–122.

Harrop, et al., 1994, "Isolation of Cysteine Proteinase Genes from Nematodes", *Struct. Mol. Biol. Protease Function and Inhibition*, (S413):167.

Karanu, et al., 1993, "*Haemonchus contortus*: Identification of Proteases with Diverse Characteristics in Adult Worm Excretory-Secretory Products", *Experimental Parasitology*, 77:362–371.

Knox et al., 1993, "Characterization of proteinases in extracts of adult *Haemonchus contortus*, nematode", *Parasitology*, 106:395–404.

McKerrow, J., 1994, "Cysteine proteases of parasites: A remarkable diversity of function", *Perspectives, in Drug Discovery and Design*, 2:437–444.

McKerrow, J., 1989, "Minireview: Parasite Proteases", *Experimental Parasitology*, 68:111–115.

Stadnyk, et al., 1990, "The acute-phase protein response in parasite infection. *Nippostrongylus brasiliensis* and *Trichinella spiralis* in the rat", *Immunology*, 69:588–595.

Tang, et al., 1992, "Genetic immunization is a simple method for eliciting an immune response", *Nature*, 356:152–154.

FILARIID NEMATODE CYSTEINE PROTEASE PROTEINS

This application is a continuation of U.S. application Ser. No. 08/249,552, filed May 26, 1994, entitled "Novel Parasite Protease Genes and Protein", now abandoned.

FIELD OF THE INVENTION

The present invention relates to novel parasite protease genes, proteins encoded by such genes, antibodies raised against such proteins, and protease inhibitors produced using such proteins. Particular proteases of the present invention include astacin metalloendopeptidases and cysteine proteases. The present invention also includes therapeutic compositions comprising such nucleic acid molecules, proteins, antibodies and inhibitors, as well as their use to protect animals from disease caused by parasites, such as by tissue-migrating helminths such as heartworm.

BACKGROUND OF THE INVENTION

Parasite infections in animals, including humans, are typically treated by chemical drugs, because there are essentially no efficacious vaccines available. One disadvantage with chemical drugs is that they must be administered often. For example, dogs susceptible to heartworm are typically treated monthly to maintain protective drug levels. Repeated administration of drugs to treat parasite infections, however, often leads to the development of resistant strains that no longer respond to treatment. Furthermore, many of the chemical drugs are harmful to the animals being treated, and as larger doses become required due to the build up of resistance, the side effects become even greater.

It is particularly difficult to develop vaccines against parasite infections both because of the complexity of the parasite's life cycle and because, while administration of parasites or parasite antigens can lead to the production of a significant antibody response, the immune response is typically not sufficient to protect the animal against infection.

As for most parasites, the life cycle of *Dirofilaria immitis*, the helminth that causes heartworm, includes a variety of life forms, each of which presents different targets, and challenges, for immunization. Adult forms of the parasite are quite large and preferentially inhabit the heart and pulmonary arteries of an animal. Males worms are typically about 12 centimeters (cm) to about 20 cm long and about 0.7 millimeters (mm) to about 0.9 mm wide; female worms are about 25 cm to about 31 cm long and about 1.0 to about 1.3 mm wide. Sexually mature adults, after mating, produce microfilariae which are only about 300 micrometers (µm) long and about 7 µm wide. The microfilariae traverse capillary beds and circulate in the vascular system of dogs in concentrations of about $10^3$ to about $10^5$ microfilariae per milliliter (ml) of blood. One method of demonstrating infection in dogs is to detect the circulating microfilariae.

If dogs are maintained in an insect-free environment, the life cycle of the parasite cannot progress. However, when microfilariae are ingested by female mosquitos during blood feeding on an infected dog, subsequent development of the microfilariae into larvae occurs in the mosquito. The microfilariae go through two larval stages (L1 and L2) and finally become mature third stage larvae (L3) of about 1.1 mm length, which can then be transmitted back to a dog through the bite of the mosquito. It is this L3 stage, therefore, that accounts for the initial infection. As early as three days after infection, the L3 molt to the fourth larval (L4) stage, and subsequently to the fifth stage, or immature adults. The immature adults migrate to the heart and pulmonary arteries, where they mature and reproduce, thus producing the microfilariae in the blood. "Occult" infection with heartworm in dogs is defined as an infection in which no microfilariae can be detected, but the existence of adult heartworms can be determined through thoracic examination.

Both the molting process and tissue migration are likely to involve the action of one or more enzymes, including proteases. Although protease activity has been identified in a number of parasites (including in larval excretory-secretory products) as well as in mammals, there apparently has been no identification of an astacin metalloendopeptidase gene in any parasite or of a cysteine protease gene in any filariid.

*Astacin metalloendopeptidases*, so-called because of their similarity to the metalloendopeptidase astacin found in crayfish, are a relatively newly recognized class of metalloproteases that have been found in humans, mice and rats as well as apparently in Drosophila fruit flies, Xenopus frogs and sea urchins; see, for example, Gomis-Ruth et al., 1993, *J. Mol. Biol.* 229, 945–968; Jiang et al., 1992, *FEBS Letters* 312, 110–114; and Dumermuth et al., 1991, *J. Biol. Chem.* 266, 21381–21385. Human intestinal and mouse kidney brush border metalloendopeptidases share about 82 percent homology in the amino-terminal 198 amino acids. Both share about 30 percent homology with astacin and with the amino-terminal domain of human bone morphogenetic protein 1. Members of the astacin family share an extended zinc-binding domain motif, the consensus sequence of which was identified by Dumermuth et al., ibid., as being HEXXHXXGFXHE, wherein H is histidine, E is glutamic acid, G is glycine, F is phenylalanine and X can be any amino acid. Gomis-Ruth et al., ibid., define the zinc-binding domain motif as His-Glu-Uaa-Xaa-His-Xaa-Uaa-Gly-Uaa-Xaa-His, wherein Uaa is a bulky apolar residue-containing amino acid. Jiang et al., ibid., disclose not only the extended zinc-binding domain motif, which they represent as HEIGHAIGFXHE (letters in bold being strictly conserved) but also two other sequences conserved between astacin metalloendopeptidases, including RXDRD spanning amino acids from about 15 through about 19 and YDYXSIMHY spanning amino acids from about 53 through about 61, assuming that the first histidine in the extended zinc-binding domain motif is amino acid position 1. The three histidines at positions 1, 5 and 11 appear to be responsible for zinc binding as is the tyrosine at position 61. The glutamic acid at position 2 is responsible for catalysis. Other key amino acids include the glycine at position 8 which is involved in secondary structure and the glutamic acid at position 12 which forms a salt bridge with the amino-terminus of the mature enzyme.

Consensus sequences, particularly around the active sites, have also been identified for serine and cysteine proteases; see, for example, Sakanari et al., 1989, *Proc. Natl. Acad. Sci. USA* 86, 4863–4867. Although cysteine protease genes have been isolated from several mammalian sources and from the nematodes *Haemonchus contortus* (e.g., Pratt et al., 1992, *Mol. Biochem. Parasitol.* 51, 209–218) and *Caenorhabditis elegans* (Ray et al., 1992, *Mol. Biochem. Parasitol.* 51, 239–250), the cloning of such genes does not necessarily predict that the cloning of novel cysteine protease genes will be straight-forward, particularly since the sequences shared by different cysteine proteases are such that probes and primers based on the consensus sequences are highly degenerative.

Heartworm not only is a major problem in dogs, which typically are unable to develop immunity after infection (i.e., dogs can become reinfected even after being cured by chemotherapy), but is also becoming increasingly widespread in other companion animals, such as cats and ferrets. Heartworm infections have also been reported in humans. Other parasite infections are also widespread, and all require better treatment, including preventative vaccine programs and/or targeted drug therapies.

SUMMARY OF THE INVENTION

One embodiment of the present invention is an isolated parasite nucleic acid molecule capable of hybridizing, under stringent conditions, with a *Dirofilaria immitis* astacin metalloendopeptidase gene. Such a nucleic acid molecule, namely a parasite astacin metalloendopeptidase nucleic acid molecule, can include a regulatory region of a parasite astacin metalloendopeptidase gene and/or encode at least a portion of a parasite astacin metalloendopeptidase protein. A preferred nucleic acid molecule of the present invention includes at least a portion of SEQ ID NO:1 and/or of SEQ ID NO:2. The present invention also includes recombinant molecules and recombinant cells that include parasite astacin metalloendopeptidase nucleic acid molecules of the present invention. Also included are methods to produce such nucleic acids, recombinant molecules and recombinant cells of the present invention.

Another embodiment of the present invention is an isolated protein that includes a parasite astacin metalloendopeptidase protein or a mimetope of such a protein. A parasite astacin metalloendopeptidase protein of the present invention preferably has astacin metalloendopeptidase activity and/or comprises a protein that, when administered to an animal in an effective manner, is capable of eliciting an immune response against a natural parasite astacin metalloendopeptidase protein. The present invention also includes inhibitors of astacin metalloendopeptidase activity as well as antibodies that recognize, (i.e., selectively bind to) a parasite astacin metalloendopeptidase protein and/or mimetope thereof of the present invention. Also included are methods to produce such proteins, inhibitors and antibodies of the present invention.

Yet another embodiment of the present invention is an isolated filariid nematode nucleic acid molecule capable of hybridizing, under stringent conditions, with a *D. immitis* cysteine protease gene. Such a nucleic acid molecule, namely a filariid cysteine protease nucleic acid molecule, can include a regulatory region of a filariid cysteine protease gene and/or encode at least a portion of a filariid cysteine protease protein. A preferred nucleic acid molecule of the present invention includes at least a portion of SEQ ID NO:12. The present invention also includes recombinant molecules and recombinant cells that include filariid cysteine protease nucleic acid molecules of the present invention. Also included are methods to produce such nucleic acids, recombinant molecules and recombinant cells of the present invention.

Another embodiment of the present invention is an isolated protein that includes a filariid cysteine protease protein or a mimetope of such a protein. A filariid cysteine protease protein of the present invention preferably has cysteine protease activity and/or comprises a protein that, when administered to an animal in an effective manner, is capable of eliciting an immune response against a natural filariid cysteine protease protein. The present invention also includes inhibitors of cysteine protease activity as well as antibodies that recognize (i.e., selectively bind to) a filariid cysteine protease protein and/or mimetope thereof of the present invention. Also included are methods to produce such proteins, inhibitors and antibodies of the present invention.

Yet another embodiment of the present invention is a therapeutic composition capable of protecting an animal from disease caused by a parasite. Such a therapeutic composition includes at least one of the following protective compounds: an isolated parasite astacin metalloendopeptidase protein or a mimetope thereof; an isolated parasite nucleic acid molecule capable of hybridizing under stringent conditions with a *D. immitis* astacin metalloendopeptidase gene; an anti-parasite astacin metalloendopeptidase antibody; an inhibitor of astacin metalloendopeptidase activity identified by its ability to inhibit parasite astacin metalloendopeptidase activity; an isolated filariid nematode cysteine protease protein or a mimetope thereof; an isolated filariid nematode nucleic acid molecule capable of hybridizing under stringent conditions with a *D. immitis* cysteine protease gene; an anti-filariid nematode cysteine protease antibody; and an inhibitor of cysteine protease activity identified by its ability to inhibit filariid nematode cysteine protease activity. Also included is a method to protect an animal from disease caused by a parasite that includes administering to the animal in an effective manner a therapeutic composition of the present invention. A preferred therapeutic composition of the present invention is a composition capable of protecting an animal from heartworm.

The present invention also includes a method to identify a compound capable of inhibiting astacin metalloendopeptidase activity of a parasite. Such a method includes (a) contacting an isolated parasite astacin metalloendopeptidase protein with a putative inhibitory compound under conditions in which, in the absence of the compound, the astacin metalloendopeptidase protein has astacin metalloendopeptidase activity; and (b) determining if the putative inhibitory compound inhibits astacin metalloendopeptidase activity. Also included is a test kit to identify a compound capable of inhibiting astacin metalloendopeptidase activity that includes an isolated parasite astacin metalloendopeptidase protein having astacin metalloendopeptidase activity and a means for determining the extent of inhibition of astacin metalloendopeptidase activity in the presence of a putative inhibitory compound.

Also included in the present invention is a method to identify a compound capable of inhibiting cysteine protease activity of a parasite. Such a method includes (a) contacting an isolated filariid cysteine protease protein with a putative inhibitory compound under conditions in which, in the absence of the compound, the filariid cysteine protease protein has cysteine protease activity; and (b) determining if the putative inhibitory compound inhibits cysteine protease activity. Also included is a test kit to identify a compound capable of inhibiting cysteine protease activity of a parasite that includes an isolated filariid cysteine protease protein having cysteine protease activity and a means for determining the extent of inhibition of cysteine protease activity in the presence of a putative inhibitory compound.

DETAILED DESCRIPTION OF THE INVENTION

The present invention includes the discovery that parasites such as *D. immitis* express astacin metalloendopeptidases. As such, the present invention includes nucleic acid molecules encoding such proteins as well as the proteins themselves. To the inventors' knowledge, astacin metalloendopeptidases have been found previously only in humans, mice, rats, crayfish, Drosophila, Xenopus and sea urchins. The present invention also includes the first identification and isolation of nucleic acid molecules encoding filariid nematode cysteine proteases as well as the cysteine proteases themselves, after a difficult and time-consuming search by the inventors for such nucleic acid molecules. Isolated nucleic acid molecules and proteins of the present invention, including homologues of such nucleic acid molecules and proteins, are useful both in protecting animals from parasite infections and in other applications, including those disclosed below.

One embodiment of the present invention is an isolated parasite (or parasitic) astacin metalloendopeptidase protein or a mimetope thereof (i.e., a mimetope of a parasite astacin metalloendopeptidase protein). According to the present invention, an isolated, or biologically pure, protein, is a protein that has been removed from its natural milieu. As such, "isolated" and "biologically pure" do not necessarily reflect the extent to which the protein has been purified. An isolated parasite astacin metalloendopeptidase protein can be obtained from its natural source. Such an isolated protein can also be produced using recombinant DNA technology or chemical synthesis.

As used herein, an isolated parasite astacin metalloendopeptidase protein can be a full-length protein or any homologue of such a protein, such as a protein in which amino acids have been deleted (e.g., a truncated version of the protein, such as a peptide), inserted, inverted, substituted and/or derivatized (e.g., by glycosylation, phosphorylation, acetylation, myristylation, prenylation, palmitation, amidation and/or addition of glycosylphosphatidyl inositol) such that the homologue has astacin metalloendopeptidase activity and/or is capable of eliciting an immune response against a natural D. immitis astacin metalloendopeptidase protein. As used herein, an astacin metalloendopeptidase protein, the full-length version of which is a protein that includes an extended zinc-binding domain, has characteristics similar to astacin and other members of the "astacin family of metalloendopeptidases"; see, for example, Dumermuth et al., ibid. A protein having astacin metalloendopeptidase activity is a protein that can cleave proteins in a manner similar to the zinc-dependent protease astacin. Astacin activity is inhibited by metal chelators such as ethylene diamine tetraacetic acid (EDTA) and 1,10-phenanthroline but not by phosphoramidon, an inhibitor of several other metalloproteases including thermolysin and neutral endopeptidases. Such an activity can be detected by those skilled in the art (see, for example, Dumermuth et al., ibid.). A protein capable of eliciting an immune response against a natural protein is a protein that includes at least one epitope capable of eliciting an immune response (humoral and/or cellular) against that natural protein (such as a D. immitis astacin metalloendopeptidase or a D. immitis cysteine protease) when the protein (e.g., the natural protein or a homologue thereof) is administered to an animal as an immunogen using techniques known to those skilled in the art. The ability of a protein to effect an immune response can be measured using techniques known to those skilled in the art. Examples of methods to measure an immune response (e.g., antibody detection, resistance to infection) are disclosed herein.

A parasite astacin metalloendopeptidase protein of the present invention, including a homologue of the full-length protein, has the further characteristic of being encoded by a nucleic acid molecule that is capable of hybridizing, under stringent conditions, with (i.e., to) a D. immitis astacin metalloendopeptidase gene. A preferred astacin metalloendopeptidase protein of the present invention is capable of hybridizing, under stringent conditions, with at least a portion of the nucleic acid sequence disclosed in SEQ ID NO:1 and/or SEQ ID NO:2. As used herein, the phrase "at least a portion of" an entity refers to an amount of the entity that is at least sufficient to have the functional aspects of that entity. For example, at least a portion of a nucleic acid sequence, as used herein, is an amount of a nucleic acid sequence capable of forming a stable hybrid under stringent hybridization conditions. As used herein, stringent hybridization conditions refer to standard hybridization conditions under which nucleic acid molecules (or sequences), including oligonucleotides, are used to identify similar sequences. Such standard conditions are disclosed, for example, in Sambrook et al., Molecular Cloning: A Laboratory Manual, Cold Spring Harbor Labs Press, 1989. Examples of such conditions are provided in the Examples section. It should be noted that the extent of homology required to form a stable hybrid can vary depending on whether the homologous sequences are interspersed throughout the nucleic acid molecules or are clustered (i.e., localized) in distinct regions on the nucleic acid molecules. Also in accordance with present invention, at least a portion of a astacin metalloendopeptidase protein is a protein of sufficient size to have astacin metalloendopeptidase activity and/or to be able to elicit an immune response against a natural parasite astacin metalloendopeptidase.

SEQ ID NO:1 and SEQ ID NO:2 represent the deduced sequences of two cDNA (complementary DNA) nucleic acid molecules denoted $nDiMPA1_{1299}$ and $nDiMPA2_{2126}$, respectively, the production of which is disclosed in the Examples. It should be noted that since nucleic acid sequencing technology is not entirely error-free, SEQ ID NO:1 and SEQ ID NO:2 represent, at best, apparent nucleic acid sequences of the respective nucleic acid molecules. As will be discussed in greater detail below, nucleic acid molecules $nDiMPA1_{1299}$ and $nDiMPA2_{2126}$ apparently comprise overlapping open reading frames, as deduced from SEQ ID NO:1 and SEQ ID NO:2.

Nucleic acid molecule $nDiMPA1_{1299}$ apparently comprises three open reading frames, referred to herein as $PDiMPA1_{ORF1}$, $PDiMPA1_{ORF2}$ and $PDiMPA1_{ORF3}$, the deduced amino acid sequences of which are disclosed, respectively, in SEQ ID NO:3, SEQ ID NO:4 and SEQ ID NO:5. Nucleic acid molecule $nDiMPA2_{2126}$ apparently comprises five open reading frames, referred to herein as $PDiMPA2_{ORF1}$, $PDiMPA2_{ORF2}$, $PDiMPA2_{ORF3}$, $PDiMPA2_{ORF4}$ and $PDiMPA2_{ORF5}$, the deduced amino acid sequences of which are disclosed, respectively, in SEQ ID NO:6, SEQ ID NO:7, SEQ ID NO:8, SEQ ID NO:9 and SEQ ID NO:10. That the open reading frames on both nucleic acid molecules are overlapping raises the possibility that translation of a functional astacin metalloendopeptidase in vivo may involve frameshifting. Both SEQ ID NO:1 and SEQ ID NO:2 contain nucleic acid sequences, including stem-loop structures, that, for frameshift viral gene expression, have been implicated in ribosome slowing and, hence, frameshift translation. Nucleic acid molecules $nDiMPA1_{1299}$ and $nDiMPA2_{2126}$ may also be the result of alternative splicing patterns.

SEQ ID NO:11 represents a composite amino acid sequence derived from the five open reading frames encoded by $nDiMPA2_{2126}$. As such, SEQ ID NO:11 is an example of a combination of disclosed open reading frames, in this case a combination of $PDiMPA2_{ORF1}$, $PDiMPA2_{ORF2}$, $PDiMPA2_{ORF3}$, $PDiMPA2_{ORF4}$ and $PDiMPA2_{ORF5}$. The astacin domain of SEQ ID NO:11 has about 29 percent amino acid sequence homology (i.e., identity within comparable regions) with the amino acid sequence of crayfish astacin. As used herein, an astacin domain is an amino acid sequence of about 200 amino acids that shares significant homology with crayfish astacin, which is a 200-amino acid protein. The astacin domain of SEQ ID NO:11 spans from about amino acid positions 99 through 296. The astacin domain of SEQ ID NO:11 also shares about 30 percent, 31 percent, 33 percent and 33 percent homology at the amino acid level with the astacin domains of, respectively, human bone morphogenetic protein 1, mouse kidney brush border metalloendopeptidase, human intestinal brush border metalloendopeptidases and *Xenopus laevis* embryonic protein UVS.2 (using sequences provided in Dumermuth et al., ibid.).

A preferred astacin metalloendopeptidase protein of the present invention includes an amino acid sequence having at least about 35 percent, more preferably at least about 45 percent, even more preferably at least about 60 percent and even more preferably at least about 75 percent, amino acid homology with the astacin domain of SEQ ID NO:11 (i.e., with the corresponding regions of the astacin domain of SEQ ID NO:11). A more preferred astacin metalloendopeptidase protein of the present invention includes at least a portion of at least one of the following open reading frames: PDiMPA1$_{ORF1}$, PDiMPA1$_{ORF2}$, PDiMPA1$_{ORF3}$, PDiMPA2$_{ORF1}$, PDiMPA2$_{ORF2}$, PDiMPA2$_{ORF3}$, PDiMPA2$_{ORF4}$ and PDiMPA2$_{ORF5}$, the deduced amino acid sequences of which are disclosed, respectively, in SEQ ID NO:3, SEQ ID NO:4, SEQ ID NO:5, SEQ ID NO:6, SEQ ID NO:7, SEQ ID NO:8, SEQ ID NO:9 and SEQ ID NO:10.

Preferred astacin metalloendopeptidase proteins of the present invention include an extended zinc-binding domain motif. More preferred astacin metalloendopeptidase proteins also contain the tyrosine zinc binding amino acid-containing domain as identified by Jiang et al., ibid, and disclosed above.

Parasite astacin metalloendopeptidase protein homologues can be the result of natural allelic variation or natural mutation. Homologues can also be produced using techniques known in the art including, but not limited to, direct modifications to the protein or modifications to the gene encoding the protein using, for example, classic or recombinant DNA techniques to effect random or targeted mutagenesis. Isolated astacin metalloendopeptidase proteins of the present invention, including homologues, can be identified in a straight-forward manner by the proteins' ability to effect astacin metalloendopeptidase activity and/or to elicit an immune response against parasite astacin metalloendopeptidase proteins. Examples of such identification techniques are disclosed herein.

The minimum size of an isolated protein of the present invention is sufficient to form an epitope, a size that is typically at least from about 7 to about 9 amino acids. As is appreciated by those skilled in the art, an epitope can include amino acids that naturally are contiguous to each other as well as amino acids that, due to the tertiary structure of the natural protein, are in sufficiently close proximity to form an epitope.

Any parasite astacin metalloendopeptidase is a suitable protein of the present invention. Suitable parasites from which to isolate proteins (including isolation of the natural protein or production of the protein by recombinant or synthetic techniques) include parasitic helminths, protozoa and ectoparasites such as, but not limited to nematodes, cestodes, trematodes, fleas, flies, ticks, lice, true bugs, and protozoa of the genera Babesia, Cryptosporidium, Eimeria, Encephalitozoon, Hepatozoon, Isospora, Leishmania, Neospora, Nosema, Plasmodium, Pneumocystis, Theileria, Toxoplasma and Trypanosoma. Preferred parasites include tissue-migrating parasitic helminths, and particularly tissue-migrating nematodes. Preferred nematodes include filariid, ascarid, strongyle and trichostrongyle nematodes. Particularly preferred tissue-migrating nematodes include parasites of the genera Acanthocheilonema, Aelurostrongylus, Ancylostoma, Angiostrongylus, Ascaris, Brugia, Bunostomum, Dictyocaulus, Dioctophyme, Dipetalonema, Dirofilaria, Dracunculus, Filaroides, Lagochilascaris, Loa, Mansonella, Muellerius, Necator, Onchocerca, Parafilaria, Parascaris, Protostrongylus, Setaria, Stephanofilaria, Strongyloides, Strongylus, Thelazia, Toxascaris, Toxocara, Trichinella, Uncinaria and Wuchereria. Other particularly preferred nematodes include parasites of the genera Capillaria, Chabertia, Cooperia, Enterobius, Haemonchus, Nematodirus, Oesophagostomum, ostertagia, Trichostrongylus and Trichuris. Preferred filariid nematodes include Dirofilaria, Acanthocheilonema, Brugia, Dipetalonema, Loa, Onchocerca, Parafilaria, Setaria, Stephanofilaria and Wuchereria filariid nematodes. A particularly preferred parasite is a nematode of the genus Dirofilaria, with *D. immitis*, the parasite that causes heartworm, being even more preferred.

In accordance with the present invention, a mimetope of a protein refers to any compound that is able to mimic the activity of that protein, often because the mimetope has a structure that mimics the protein. For example, a mimetope of a parasite astacin metalloendopeptidase protein is a compound that has an activity similar to that of an isolated parasite astacin metalloendopeptidase protein of the present invention. Mimetopes can be, but are not limited to: peptides that have been modified to decrease their susceptibility to degradation; anti-idiotypic and/or catalytic antibodies, or fragments thereof; non-proteinaceous immunogenic portions of an isolated protein (e.g., carbohydrate structures); and synthetic or natural organic molecules, including nucleic acids. Such mimetopes can be designed using computer-generated structures of proteins of the present invention. Mimetopes can also be obtained by generating random samples of molecules, such as oligonucleotides, peptides or other organic molecules, and screening such samples by affinity chromatography techniques using, for example, antibodies raised against a protein of the present invention.

A preferred parasite astacin metalloendopeptidase protein or mimetope of the present invention is a compound that when administered to an animal in an effective manner, is capable of protecting that animal from disease caused by a parasite that is susceptible to treatment to inhibit astacin metalloendopeptidase activity. As such, the parasite preferably is essentially incapable of causing disease in an animal that is immunized with a parasite astacin metalloendopeptidase protein, and preferably with a *D. immitis* astacin metalloendopeptidase protein, of the present invention. In accordance with the present invention, the ability of a protein or mimetope of the present invention to protect an animal from disease by a parasite refers to the ability of that protein or mimetope to treat, ameliorate and/or prevent disease, including infection leading to disease, caused by the parasite, preferably by eliciting an immune response against the parasite. Such an immune response can include humoral and/or cellular immune responses. Suitable parasites to target include any parasite that is essentially incapable of causing disease in an animal administered a parasite astacin metalloendopeptidase protein of the present invention. As such, a parasite to target includes any parasite that produces a protein having one or more epitopes that can be targeted by a humoral and/or cellular response against a parasite astacin metalloendopeptidase protein of the present invention and/or that can be targeted by a compound that is capable of substantially inhibiting parasite astacin metalloendopeptidase activity, thereby resulting in the reduced ability of the parasite to cause disease in an animal. Suitable and preferred parasites to target include those parasites disclosed above. A preferred class of parasites to target include tissue-migrating parasitic helminths. A particularly preferred nematode helminth to target is *D. immitis*, which causes heartworm.

One embodiment of the present invention is a fusion protein that includes a parasite astacin metalloendopeptidase domain attached to a fusion segment. Inclusion of a fusion segment as part of a protein of the present invention can enhance the protein's stability during production, storage and/or use. Depending on the segment's characteristics, a fusion segment can also act as an immunopotentiator to enhance the immune response mounted by an animal immunized with a protein of the present invention that contains such a fusion segment. Furthermore, a fusion segment can function as a tool to simplify purification of a protein of the present invention, such as to enable purification of the resultant fusion protein using affinity chromatography. A suitable fusion segment can be a domain of any size that has the desired function (e.g., imparts increased stability to a protein, imparts increased immunogenicity to a protein, and/or simplifies purification of a protein). It is within the scope of the present invention to use one or more fusion segments. Fusion segments can be joined to amino and/or carboxyl termini of the astacin metalloendopeptidase-containing domain of the protein. Linkages between fusion segments and astacin metalloendopeptidase-containing domains of fusion proteins can be susceptible to cleavage in order to enable straight-forward recovery of the astacin metalloendopeptidase-containing domains of such proteins. Fusion proteins are preferably produced by culturing a recombinant cell transformed with a fusion nucleic acid molecule that encodes a protein including the fusion segment attached to either the carboxyl and/or amino terminal end of an parasite astacin metalloendopeptidase-containing domain.

Preferred fusion segments for use in the present invention include a glutathione binding domain, such as *Schistosoma japonicum* glutathione-S-transferase (GST) or a portion thereof capable of binding to glutathione; a metal binding domain, such as a poly-histidine segment capable of binding to a divalent metal ion; an immunoglobulin binding domain, such as Protein A, Protein G, T cell, B cell, Fc receptor or complement protein antibody-binding domains; a sugar binding domain such as a maltose binding domain from a maltose binding protein; and/or a "tag" domain (e.g., at least a portion of β-galactosidase, a strep tag peptide, other domains that can be purified using compounds that bind to the domain, such as monoclonal antibodies). More preferred fusion segments include metal binding domains, such as a poly-histidine segment; a maltose binding domain; a strep tag peptide, such as that available from Biometra in Tampa, Fla.; and an S10 peptide. An example of a preferred fusion protein of the present invention is PHIS-PDiMPA2$_{804}$, the production of which is disclosed herein.

Another embodiment of the present invention is a parasite astacin metalloendopeptidase protein that also includes at least one additional protein segment that is capable of protecting an animal from one or more diseases. Such a multivalent protective protein can be produced by culturing a cell transformed with a nucleic acid molecule comprising two or more nucleic acid domains joined together in such a manner that the resulting nucleic acid molecule is expressed as a multivalent protective compound containing at least two protective compounds, or portions thereof, capable of protecting an animal from diseases caused, for example, by at least one infectious agent.

Examples of multivalent protective compounds include, but are not limited to, a parasite astacin metalloendopeptidase protein attached to one or more other parasite proteins, such to a filariid nematode cysteine protease protein of the present invention. Other examples of multivalent protective compounds include a parasite astacin metalloendopeptidase protein attached to one or more compounds protective against one or more other infectious agents, particularly an agent that infects cats or dogs, such as, but not limited to, calicivirus, distemper virus, feline herpesvirus, feline immunodeficiency virus, feline leukemia virus, feline infectious peritonitis, hepatitis, hookworm, leptospirosis, panleukopenia virus, parvovirus, rabies and toxoplasmosis.

Suitable heartworm multivalent protective proteins include, but are not limited to, a *D. immitis* astacin metalloendopeptidase and/or a *D. immitis* cysteine protease of the present invention attached to at least one other *D. immitis* protein such as, but not limited to, a *D. immitis* Gp29 protein, a *D. immitis* P39 protein, a *D. immitis* P22U protein, a *D. immitis* P22L protein, a *D. immitis* P20.5 protein, a *D. immitis* P4 protein, a *D. immitis* Di22 protein and/or a *D. immitis* protease expressed in L3 and/or L4 larvae, as well as other helminth proteins sharing significant homology with such *D. immitis* proteins. A protein sharing significant homology with another protein refers to the ability of the nucleic acid sequences encoding such proteins to form stable hybridization complexes with each other under stringent hybridization conditions, as described, for example, in Sambrook et al., ibid. U.S. patent application Ser. No. 08/208, 885, filed Mar. 8, 1994, entitled "*D. immitis* Gp29 Proteins, Nucleic Acid Molecules and Uses Thereof", discloses *D. immitis* Gp29 proteins and nucleic acid molecules that encode them. U.S. patent application Ser. No. 08/003,389, filed Jan. 12, 1993, entitled "Immunoaenic Larval Proteins", discloses a 39-kD (kilodalton) *D. immitis* protein (size determined by Tris glycine SDS-PAGE (sodium dodecyl sulfate polyacrylamide gel electrophoresis)), referred to herein as P39, and a nucleic acid sequence that encodes it. U.S. patent application Ser. No. 08/003,257, filed Jan. 12, 1993, entitled "Reagents and Methods for Identification of Vaccines", discloses 22-kD and 20.5-kD *D. immitis* proteins (sizes determined by Tris glycine SDS-PAGE), referred to herein as P22L and P20.5, and nucleic acid sequences that encode them. U.S. patent application Ser. No. 08/109,391, filed Aug. 19, 1993, entitled "Novel Parasitic Helminth Proteins", discloses *D. immitis* P4 and *D. immitis* P22U, as well as nucleic acid sequences that encode them. U.S. patent application Ser. No. 08/060,500, filed May 10, 1993, entitled "Heartworm Vaccine", discloses a *D. immitis* Di22 protein and a nucleic acid sequence encoding it (included in Genbank data base accession number M82811); Ser. No. 08/060, 500 is a continuation of U.S. patent application Ser. No. 07/683,202, filed Apr. 8, 1991. U.S. patent application Ser. No. 08/153,554, filed Nov. 16, 1993, entitled "Protease Vaccine Against Heartworm", discloses *D. immitis* larval proteases; Ser. No. 08/153,554 is a continuation of U.S. patent application Ser. No. 07/792,209, filed Nov. 12, 1991. The specification of U.S. patent application Ser. No. 07/792, 209 and Ser. No. 08/153,554 was published as PCT Application No. PCT/US92/09702. Each of these patent applications is incorporated by reference herein in its entirety.

A particularly preferred parasite astacin metalloendopeptidase protein is a protein encoded by at least a portion of SEQ ID NO:1 or SEQ ID NO:2, and, as such, is a protein having an amino acid sequence that includes at least a portion of at least one of the open reading frames represented by, respectively, SEQ ID NO:3, SEQ ID NO:4, SEQ ID NO:5, SEQ ID NO:6, SEQ ID NO:7, SEQ ID NO:8, SEQ ID NO:9 and SEQ ID NO:10. Preferred proteins can include combinations of such reading frames, such as SEQ ID No:11, that result in a functional protein. A homology search using these open reading frames indicate that all but SEQ ID NO:10 share significant homology with known members of the astacin metalloendopeptidase family and with a *Caenorhabditis elegans* R151.5 gene product, Genbank accession number U00036 (Wilson et al., 1994, *Nature* 368, 32–38), suggesting that *C. elegans* also encodes a astacin metalloendopeptidase. Particularly well conserved are the extended zinc-binding domain motif and the tyrosine-containing domain motif, the overall sequence homology being about 24 percent.

Particularly preferred proteins of the present invention include proteins having the astacin domain of SEQ ID NO:11, proteins that include that domain (such as, but not limited to, full-length proteins, fusion proteins and proteins providing multivalent protection) and proteins that are truncated homologues of that domain. Even more preferred proteins include PDiMPA2$_{804}$ and PHIS-PDiMPA2$_{804}$.

Another embodiment of the present invention is an isolated parasite nucleic acid molecule capable of hybridizing, under stringent conditions, with a *D. immitis* astacin metalloendopeptidase gene. As used herein, a *D. immitis* astacin metalloendopeptidase gene includes all nucleic acid sequences related to a natural *D. immitis* astacin metalloendopeptidase gene such as regulatory regions that control production of a *D. immitis* astacin metalloendopeptidase protein encoded by that gene (such as, but not limited to, transcription, translation or post-translation control regions) as well as the coding region itself. A parasite astacin metalloendopeptidase nucleic acid molecule of the present invention can include any isolated natural parasite astacin metalloendopeptidase gene or a homologue thereof. A nucleic acid molecule of the present invention can include one or more regulatory regions, full-length or partial coding regions, or combinations thereof. The minimal size of a parasite astacin metalloendopeptidase nucleic acid molecule of the present invention is the minimal size capable of forming a stable hybrid under stringent hybridization conditions. Suitable and preferred parasites are disclosed above.

In accordance with the present invention, an isolated nucleic acid molecule is a nucleic acid molecule that has been removed from its natural milieu (i.e., that has been subject to human manipulation). As such, "isolated" does not reflect the extent to which the nucleic acid molecule has been purified. An isolated nucleic acid molecule can include DNA, RNA, or derivatives of either DNA or RNA.

An isolated parasite astacin metalloendopeptidase nucleic acid molecule of the present invention can be obtained from its natural source either as an entire (i.e., complete) gene or a portion thereof capable of forming a stable hybrid with that gene. An isolated parasite astacin metalloendopeptidase nucleic acid molecule can also be produced using recombinant DNA technology (e.g., polymerase chain reaction (PCR) amplification, cloning) or chemical synthesis. Isolated parasite astacin metalloendopeptidase nucleic acid molecules include natural nucleic acid molecules and homologues thereof, including, but not limited to, natural allelic variants and modified nucleic acid molecules in which nucleotides have been inserted, deleted, substituted, and/or inverted in such a manner that such modifications do not substantially interfere with the nucleic acid molecule's ability to encode a parasite astacin metalloendopeptidase protein of the present invention or to form stable hybrids under stringent conditions with natural isolates.

A parasite astacin metalloendopeptidase nucleic acid molecule homologue can be produced using a number of methods known to those skilled in the art (see, for example, Sambrook et al., ibid.). For example, nucleic acid molecules can be modified using a variety of techniques including, but not limited to, classic mutagenesis techniques and recombinant DNA techniques, such as site-directed mutagenesis, chemical treatment of a nucleic acid molecule to induce mutations, restriction enzyme cleavage of a nucleic acid fragment, ligation of nucleic acid fragments, polymerase chain reaction (PCR) amplification and/or mutagenesis of selected regions of a nucleic acid sequence, synthesis of oligonucleotide mixtures and ligation of mixture groups to "build" a mixture of nucleic acid molecules and combinations thereof. Nucleic acid molecule homologues can be selected from a mixture of modified nucleic acids by screening for the function of the protein encoded by the nucleic acid (e.g., astacin metalloendopeptidase activity or ability to elicit an immune response against at least one epitope of a parasite astacin metalloendopeptidase protein) and/or by hybridization with isolated parasite astacin metalloendopeptidase nucleic acids under stringent conditions.

An isolated nucleic acid molecule of the present invention can include a nucleic acid sequence that encodes at least one parasite astacin metalloendopeptidase protein of the present invention, examples of such proteins being disclosed herein. Although the phrase "nucleic acid molecule" primarily refers to the physical nucleic acid molecule and the phrase "nucleic acid sequence" primarily refers to the sequence of nucleotides on the nucleic acid molecule, the two phrases can be used interchangeably, especially with respect to a nucleic acid molecule, or a nucleic acid sequence, being capable of encoding a protein. As heretofore disclosed, parasite astacin metalloendopeptidase proteins of the present invention include, but are not limited to, proteins having full-length astacin metalloendopeptidase coding regions, proteins having partial astacin metalloendopeptidase coding regions, fusion proteins, multivalent protective proteins and combinations thereof.

One embodiment of the present invention is a parasite astacin metalloendopeptidase nucleic acid molecule that is capable of hybridizing under stringent conditions with nucleic acid molecule nDiMPA1$_{1299}$ and/or with nucleic acid molecule nDiMPA2$_{2126}$. As such, preferred astacin metalloendopeptidase nucleic acid molecules are capable of forming stable hybrids with nucleic acid molecules represented by SEQ ID NO:1 and SEQ ID NO:2. Particularly preferred astacin metalloendopeptidase nucleic acid molecules comprise at least a portion of nucleic acid molecule nDiMPA1$_{1299}$ and/or nucleic acid molecule nDiMPA2$_{2126}$. As such, a preferred nucleic acid molecule of the present invention includes a nucleic acid sequence including at least a portion of SEQ ID NO:1 OR SEQ ID NO:2. Such a nucleic acid molecule can be nDiMPA1$_{1299}$ or nDiMPA2$_{2126}$, can include nucleotides in addition to nDiMPA1$_{1299}$ or nDiMPA2$_{2126}$, or can be a truncation fragment of nDiMPA1$_{1299}$ or nDiMPA2$_{2126}$. Particularly preferred nucleic acid molecules include nDiMPA1$_{689}$, nDiMPA1$_{1299}$, nDiMPA2$_{2126}$, nDiMPA2$_{804}$, nDiMPA2$_{271}$ and BvMPA2, the production of which is disclosed in the Examples.

One preferred embodiment of the present invention is a parasite astacin metalloendopeptidase nucleic acid molecule capable of hybridizing to a nucleic acid molecule encoding at least one of the following open reading frames as denoted by the following amino acid sequences: SEQ ID NO:3, SEQ ID NO:4, SEQ ID NO:5, SEQ ID NO:6, SEQ ID NO:7, SEQ ID NO:8, SEQ ID NO:9, SEQ ID NO:10 AND SEQ ID NO:11. Preferably, such a nucleic acid molecule encodes a protein that shares at least about 35 percent, more preferably at least about 45 percent, even more preferably at least about 60 percent and even more preferably at least about 75 percent amino acid homology with SEQ ID NO:11. More preferred astacin metalloendopeptidase nucleic acid molecules encode at least a portion of at least one of such open reading frames. Particularly preferred astacin metalloendopeptidase nucleic acid molecules are capable of forming stable hybrids with nucleic acid molecules encoding an extended zinc-binding domain motif (i.e., to the carboxyl terminus of the motif as well as to the general zinc-binding domain) and, more preferably, also with nucleic acid molecules encoding other disclosed conserved domains of astacin metalloendopeptidases, such as the motif that contains the tyrosine believed to bind to zinc.

Knowing the nucleic acid sequence of certain parasite astacin metalloendopeptidase nucleic acid molecules of the present invention allows one skilled in the art to make copies of those nucleic acid molecules as well as to obtain nucleic acid molecules including at least a portion of such nucleic acid molecules and other parasite astacin metalloendopeptidase nucleic acid molecule homologues. Such nucleic acid molecules can be obtained in a variety of ways including screening appropriate expression libraries with antibodies of the present invention; traditional cloning techniques using oligonucleotide probes of the present invention to screen appropriate libraries or DNA; and PCR amplification of appropriate libraries or DNA using oligonucleotide primers of the present invention. Preferred libraries to screen or from which to amplify include parasite larval (especially L3, L4) and adult cDNA libraries as well as genomic DNA libraries. Similarly, preferred DNA sources to screen or from which to amplify include parasite larval (especially L3, L4) and adult cDNA and genomic DNA. Techniques to clone and amplify genes are disclosed, for example, in Sambrook et al., ibid.

The present invention also includes nucleic acid molecules that are oligonucleotides capable of hybridizing, under stringent conditions, with complementary regions of other, preferably longer, nucleic acid molecules of the present invention, such as to complementary regions of a parasite astacin metalloendopeptidase gene, including complementary regions of a *D. immitis* astacin metalloendopeptidase gene. Such oligonucleotides can hybridize under stringent conditions with complementary regions of nDiMPA1$_{299}$ or nDiMPA2$_{2126}$, complementary regions of nucleic acid molecules that include at least a portion of nDiMPA1$_{1299}$ or nDiMPA2$_{2126}$, and complementary regions of nucleic acid molecules that hybridize under stringent conditions with nDiMPA1$_{1299}$ or nDiMPA2$_{2126}$. Such oligonucleotides can be RNA, DNA, or derivatives of either. The minimal size of such oligonucleotides is the size required to form a stable hybrid between a given oligonucleotide and the complementary sequence on another nucleic acid molecule of the present invention. As such, the size is dependent on nucleic acid composition and percent homology between the oligonucleotide and complementary sequence as well as upon hybridization conditions per se (e.g., temperature, salt concentration). For AT-rich nucleic acid sequences, such as those of parasitic helminths, oligonucleotides typically are at least about 15 to about 17 bases in length. The size of the oligonucleotide must also be sufficient for the use of the oligonucleotide in accordance with the present invention. Oligonucleotides of the present invention can be used in a variety of applications including, but not limited to, as probes to identify additional nucleic acid molecules, as primers to amplify or extend nucleic acid molecules or in therapeutic applications to inhibit, for example, expression of astacin metalloendopeptidases by a parasite. Such therapeutic applications include the use of such oligonucleotides in, for example, antisense-, triplex formation-, ribozyme- and/or RNA drug-based technologies. The present invention, therefore, includes such oligonucleotides and methods to interfere with the production of astacin metalloendopeptidase proteins by use of one or more of such technologies. Appropriate oligonucleotide-containing therapeutic compositions can be administered to an animal, using techniques known to those skilled in the art, either prior to or after infection by a parasite such as *D. immitis*, in order to protect the animal from disease.

Another embodiment of the present invention is an isolated filariid nematode cysteine protease protein or a mimetope thereof. As used herein, an isolated filariid nematode, or filariid, cysteine protease protein can be a full-length filariid cysteine protease protein or any homologue of such a protein. Filariid nematode cysteine protease proteins, including homologues thereof, can be isolated and produced according to the methods disclosed herein for parasite astacin metalloendopeptidase proteins. Homologues and mimetopes of filariid cysteine protease proteins are defined in a similar manner as are homologues and mimetopes of parasite astacin metalloendopeptidase proteins. Filariid cysteine protease proteins (including homologues) and mimetopes thereof each are capable of eliciting an immune response (i.e., having at least one epitope capable of eliciting an immune response) against a filariid cysteine protease protein and/or are capable of effecting cysteine protease activity. Cysteine protease activity, as well as the ability of a protein to effect an immune response, can be measured using techniques known to those skilled in the art. Cysteine protease activity can be measured by its ability to cleave peptides having a cysteine protease cleavage site, such as z-Val-Leu-Arg-AMC; such activity can be inhibited by, for example, by the cysteine protease inhibitor E-64 (available from Boehringer Mannheim, Indianapolis, Ind). Preferred filariids are disclosed herein. A particularly preferred filariid is *D. immitis*.

A filariid cysteine protease protein of the present invention, including any homologue thereof, has the additional characteristic of being encoded by a nucleic acid molecule that is capable of hybridizing, under stringent conditions, with a nucleic acid molecule comprising at least a portion of a nucleic acid sequence encoding a filariid cysteine protease protein. Preferred proteins are encoded by a nucleic acid molecule that forms stable hybrids with at least a portion of nDiCP$_{143}$, the production of which is described in detail in the Examples. SEQ ID NO:12 represents the deduced sequence of nDiCP$_{143}$, the deduced translation product of which is a 47 amino acid sequence represented in SEQ ID NO:13, the protein being denoted PDiCP$_{143}$. It should be noted that since nucleic acid sequencing technology is not entirely error-free, SEQ ID NO:12, at best, represents an apparent nucleic acid sequence of a nucleic acid molecule encoding at least a portion of full-length *D. immitis* cysteine protease. Furthermore, SEQ ID NO:13 apparently represents an internal amino acid sequence of *D. immitis* cysteine protease since SEQ ID NO:12 apparently has neither a start nor stop codon. SEQ ID NO:13, however, includes amino acid sequences that are conserved among a number of cysteine proteases.

A comparison of SEQ ID NO:13 with the corresponding regions of known parasite cysteine protease genes indicates that SEQ ID NO:13 shares about 16 percent, about 22 percent, about 24 percent, about 35 percent, about 39 percent, about 44 percent and about 49 percent homology at the amino acid level with cysteine proteases from, respectively, *H. contortus* (a nematode), *Schistosoma mansoni* (a trematode), *C. elegans* (a nematode), *Fasciola hepatica* (a trematode), *Entamoeba histolytica* (a protozoa) *Trypanosoma cruzi* (a protozoa) and *T. brucie*. SEQ ID NO:13 also shares about 50 percent amino acid homology with human cathepsin L, about 45 percent amino acid homology with chicken cathepsin L and about 56 percent amino acid homology with a *Paragonimus westermani* (trematode) cysteine protease. The serine at about position 30 and the cysteine at about position 37 of SEQ ID NO:13 are conserved in all of these cysteine proteases. Please see, for example, the following for listings of the above-referenced sequences: Heussler et al., 1994, *Mol. Biochem. Parasitol.* 64, 11–23; Eakin et al., 1990, *Mol. Biochem. Parasitol.* 39, 1–8; Ray et al., ibid., Pratt et al., ibid., Sakanari et al., ibid.; European Patent Application Publication No. 0524834A2, by Hamajima et al., published Jan. 27, 1993.

Preferred filariid cysteine protease proteins of the present invention include amino acid sequences that share at least about 60 percent, more preferably at least about 70 percent, and even more preferably at least about 80 percent, homology with SEQ ID NO:13. Particularly preferred filariid cysteine protease proteins of the present invention include PDiCP$_{142}$, proteins that include PDiCP$_{142}$ (including, but not limited to full-length proteins, fusion proteins and multivalent protective proteins), and proteins that include at least a portion of PDiCP$_{142}$.

A preferred filariid cysteine protease protein or mimetope thereof is a compound that when administered to an animal in an effective manner, is capable of protecting that animal from disease caused by a parasite that is susceptible to treatment with a composition that inhibits cysteine protease activity. A suitable parasite to target is any parasite that produces a protein having one or more epitopes that can be targeted by a humoral and/or cellular response against a filariid nematode cysteine protease protein of the present invention and/or that can be targeted by a compound that is capable of substantially inhibiting filariid cysteine protease activity, thereby resulting in the reduced ability of the parasite to cause disease in an animal. Suitable and preferred parasites are disclosed above. A preferred class of parasites to target include tissue-migrating parasitic helminths. A particularly preferred nematode to target is *D. immitis*, which causes heartworm.

Also included in the present invention are fusion proteins and multivalent protective proteins that include at least one filariid cysteine protease protein. Such proteins can comprise fusion segments and/or multiple protective domains similar as disclosed for parasite astacin metalloendopeptidase proteins and can be produced in a similar manner as described for parasite astacin metalloendopeptidase proteins of the present invention. Particularly preferred fusionproteins include PHIS-PDiCP$_{142}$.

Yet another embodiment of the present invention is an isolated filariid nematode nucleic acid molecule capable of hybridizing, under stringent conditions, with a *D. immitis* cysteine protease gene. Such a nucleic acid molecule is referred to as a filariid nematode, or filariid, cysteine protease nucleic acid molecule. As used herein, a filariid cysteine protease gene includes all nucleic acid sequences related to a natural filariid cysteine protease gene such as regulatory regions that control production of a *D. immitis* cysteine protease protein encoded by that gene as well as the coding region itself. A filariid cysteine protease nucleic acid molecule of the present invention can include an isolated natural filariid cysteine protease gene or a homologue thereof. A nucleic acid molecule of the present invention can include one or more regulatory regions, full-length or partial coding regions, or combinations thereof. The minimal size of a filariid cysteine protease nucleic acid molecule of the present invention is the minimal size capable of forming a stable hybrid under stringent hybridization conditions with a *D. immitis* cysteine protease gene. Filariid immitis cysteine protease nucleic acid molecules can be isolated and produced according to the methods taught herein for the production and isolation of parasite astacin metalloendopeptidase nucleic acid molecules. Cysteine protease nucleic acid molecule homologues can be selected from a mixture of modified nucleic acids by screening for the function of the protein encoded by the nucleic acid (e.g., cysteine protease activity and/or ability to elicit an immune response against at least one epitope of a filariid cysteine protease protein) and/or by hybridization with isolated *D. immitis* cysteine protease nucleic acids under stringent conditions.

An isolated filariid cysteine protease nucleic acid molecule of the present invention can include a nucleic acid sequence that encodes at least one filariid cysteine protease protein of the present invention, examples of such proteins being disclosed herein. As heretofore disclosed, filariid cysteine protease proteins of the present invention include, but are not limited to, proteins having full-length filariid cysteine protease coding regions, proteins having partial filariid cysteine protease coding regions, fusion proteins, multivalent protective proteins and combinations thereof. The present invention also includes nucleic acid molecules encoding filariid cysteine protease proteins that have been modified to accommodate codon usage properties of the cells in which such nucleic acid molecules are to be expressed.

One embodiment of the present invention is a filariid cysteine protease nucleic acid molecule that includes a nucleic acid sequence that is capable of hybridizing under stringent conditions with *D. immitis* nucleic acid molecule nDiCP$_{143}$, the deduced sequence of which is disclosed in SEQ ID NO:12. Preferred filariid cysteine protease nucleic acid molecules encode proteins having at least about 60 percent, more preferably at least about 70 percent and even more preferably at least about 80 percent, amino acid homology with SEQ ID NO:13. More preferred is a nucleic acid molecule that encodes a *D. immitis* cysteine protease protein that comprises at least a portion of SEQ ID NO:13.

A preferred nucleic acid molecule of the present invention includes at least a portion of *D. immitis* nucleic acid molecule nDiCP$_{143}$. Such a nucleic acid molecule can be nDiCP$_{143}$, can include nucleotides in addition to nDiCP$_{143}$ (such as, but not limited to, a nucleic acid molecule encoding a full-length protein, a nucleic acid molecule encoding a fusion protein, or a nucleic acid molecule encoding a multivalent protective compound), or can be a truncation fragment of nDiCP$_{143}$. Particularly preferred filariid cysteine protease nucleic acid molecules include nDiCP$_{143}$ and nDiCP$_{142}$.

The inventors of the present invention had difficulty isolating a *D. immitis* cysteine protease nucleic acid molecule despite the wide variety of cysteine protease genes that have been cloned. Primers designed by the inventors using consensus sequences derived from known cysteine protease genes, including from known parasite cysteine protease genes, had a degeneracy that was essentially too great to pull out a *D. immitis* cysteine protease gene. The inventors discovered that use of primers that incorporated *D. immitis* codon usage bias enabled the identification of the first *D. immitis* cysteine protease nucleic acid molecule, namely $nDiCP_{143}$.

Having identified the nucleic acid molecule $nDiCP_{143}$, it is likely that one skilled in the art can make copies of that nucleic acid molecule as well as obtain other filariid nematode cysteine protease nucleic acid molecules including full-length genes and homologues thereof. Such nucleic acid molecules can be obtained in a variety of ways such as those described for the isolation and production of parasite astacin metalloendopeptidase nucleic acid molecules of the present invention. Preferred libraries to screen or from which to amplify include filariid larval (especially L3, L4) and adult cDNA libraries and filariid genomic DNA libraries. Similarly, preferred DNA sources to screen or from which to amplify include filariid larval (especially L3, L4) and adult cDNA, as well as filariid genomic DNA. Preferred primers and probes to use are codon-biased for the given filariid.

The present invention also includes nucleic acid molecules that are oligonucleotides capable of hybridizing, under stringent conditions, with complementary regions of other, preferably longer, nucleic acid molecules of the present invention, such as to complementary regions of a filariid cysteine protease gene. Such oligonucleotides can hybridize under stringent conditions with complementary regions of $nDiCP_{143}$, complementary regions of nucleic acid molecules that include at least a portion of $nDiCP_{143}$, and complementary regions of nucleic acid molecules that hybridize under stringent conditions with $nDiCP_{143}$. Such oligonucleotides can be RNA, DNA, or derivatives of either. Other criteria, such as minimal size, as well as methods to produce and use such oligonucleotides are as disclosed for parasite astacin metalloendopeptidase oligonucleotides of the present invention.

The present invention also includes a recombinant vector, which includes at least one nucleic acid molecule of the present invention (e.g., a parasite astacin metalloendopeptidase nucleic acid molecule and/or a filariid cysteine protease nucleic acid molecule, examples of which are disclosed herein) inserted into any vector capable of delivering the nucleic acid molecule into a host cell. Such a vector contains heterologous nucleic acid sequences, that is nucleic acid sequences that are not naturally found adjacent to nucleic acid molecules of the present invention and that preferably are derived from a species other than the species from which the nucleic acid molecule(s) are derived. The vector can be either RNA or DNA, either prokaryotic or eukaryotic, and typically is a virus or a plasmid. Recombinant vectors can be used in the cloning, sequencing, and/or otherwise manipulating of parasite, including *D. immitis*, nucleic acid molecules of the present invention. One type of recombinant vector, herein referred to as a recombinant molecule and described in more detail below, can be used in the expression of nucleic acid molecules of the present invention. Preferred recombinant vectors are capable of replicating in the transformed cell.

Preferred nucleic acid molecules to include in recombinant vectors of the present invention include at least one of the following: a nucleic acid molecule that includes at least a portion of $nDiMPA1_{1299}$, a nucleic acid molecule that includes at least a portion of $nDiMPA2_{2126}$ and a nucleic acid molecule that includes at least a portion of $nDiCP_{143}$. Particularly preferred nucleic acid molecules to include in recombinant vectors of the present invention include $nDiMPA1_{689}$, $nDiMPA1_{1299}$, $nDiMPA2_{2126}$, $nDiMPA2_{804}$, $nDiMPA2_{271}$, BvMPA2, $nDiCP_{143}$ and $nDiCP_{142}$.

Isolated proteins of the present invention can be produced in a variety of ways, including production and recovery of natural proteins, production and recovery of recombinant proteins, and chemical synthesis of the proteins. In one embodiment, an isolated protein of the present invention is produced by culturing a cell capable of expressing the protein under conditions effective to produce the protein, and recovering the protein. A preferred cell to culture is a recombinant cell that is capable of expressing the protein, the recombinant cell being produced by transforming a host cell with one or more nucleic acid molecules of the present invention. Transformation of a nucleic acid molecule into a cell can be accomplished by any method by which a nucleic acid molecule can be inserted into the cell. Transformation techniques include, but are not limited to, transfection, electroporation, microinjection, lipofection, adsorption, and protoplast fusion. A recombinant cell may remain unicellular or may grow into a tissue, organ or a multicellular organism. Transformed nucleic acid molecules of the present invention can remain extrachromosomal or can integrate into one or more sites within a chromosome of the transformed (i.e., recombinant) cell in such a manner that their ability to be expressed is retained. A preferred nucleic acid molecule with which to transform a cell is a nucleic acid molecule that includes a parasite astacin metalloendopeptidase nucleic acid molecule and/or a filariid cysteine protease nucleic acid molecule of the present invention. Particularly preferred nucleic acid molecules with which to transform cells include $nDiMPA1_{689}$, $nDiMPA1_{1299}$, $nDiMPA2_{2126}$, $nDiMPA2_{804}$, $nDiMPA2_{271}$, BvMPA2, $nDiCP_{143}$ and $nDiCP_{142}$.

Suitable host cells to transform include any cell that can be transformed. Host cells can be either untransformed cells or cells that are already transformed with at least one nucleic acid molecule. Host cells of the present invention either can be endogenously (i.e., naturally) capable of producing parasite, including *D. immitis*, proteins of the present invention or can be capable of producing such proteins after being transformed with at least one nucleic acid molecule of the present invention. Host cells of the present invention can be any cell capable of producing at least one protein of the present invention, including bacterial, fungal (including yeast), animal parasite (including helminth, protozoa and ectoparasite), insect, animal and plant cells. Preferred host cells include bacterial, mycobacterial, yeast, helminth, insect and mammalian cells. More preferred host cells include Salmonella, Escherichia, Bacillus, Saccharomyces, Spodoptera, Mycobacteria, Trichoplusia, BHK (baby hamster kidney) cells, MDCK cells (normal dog kidney cell line for canine herpesvirus cultivation), CRFK cells (normal cat kidney cell line for feline herpesvirus cultivation) and COS cells. Particularly preferred host cells are *Escherichia coli*, including *E. coli* K-12 derivatives; *Salmonella typhi*; *Salmonella typhimurium*, including attenuated strains such as UK-1 $\chi$3987 and SR-11 $\chi$4072; *Spodoptera frugiperda*; *Trichoplusia ni*; BHK cells; MDCK cells; CRFK cells and non-tumorigenic mouse myoblast G8 cells (e.g., ATCC CRL 1246). Additional appropriate mammalian cell hosts include other kidney cell lines (e.g., CV-1 monkey kidney cell lines), other fibroblast cell lines (e.g., human, murine or chicken embryo fibroblast cell lines), myeloma cell lines, Chinese hamster ovary cells and/or HeLa cells.

A recombinant cell is preferably produced by transforming a host cell with one or more recombinant molecules, each comprising one or more nucleic acid molecules of the present invention operatively linked to an expression vector containing one or more transcription control sequences. The phrase operatively linked refers to insertion of a nucleic acid molecule into an expression vector in a manner such that the molecule is able to be expressed when transformed into a host cell. As used herein, an expression vector is a DNA or RNA vector that is capable of transforming a host cell and of effecting expression of a specified nucleic acid molecule. Preferably, the expression vector is also capable of replicating within the host cell. Expression vectors can be either prokaryotic or eukaryotic, and are typically viruses or plasmids. Expression vectors of the present invention include any vectors that function (i.e., direct gene expression) in recombinant cells of the present invention, including in bacterial, fungal, animal parasite, insect, animal, and plant cells. Preferred expression vectors of the present invention can direct gene expression in bacterial, yeast, helminth or other parasite, insect and mammalian cells and more preferably in the cell types heretofore disclosed.

Expression vectors of the present invention may also (a) contain secretory signals (i.e., signal segment nucleic acid sequences) to enable an expressed protein of the present invention (i.e., a parasite astacin metalloendopeptidase protein and/or a filariid cysteine protease protein) to be secreted from the cell that produces the protein and/or (b) contain fusion sequences which lead to the expression of inserted nucleic acid molecules of the present invention as fusion proteins. Eukaryotic recombinant molecules may include intervening and/or untranslated sequences surrounding and/ or within the nucleic acid sequences of nucleic acid molecules of the present invention. Examples of suitable fusion segments encoded by fusion segment nucleic acids have been disclosed. Suitable signal segments include natural signal segments (e.g., a parasite astacin metalloendopeptidase or cysteine protease signal segment) or any heterologous signal segment capable of directing the secretion of a protein of the present invention. Preferred signal segments include, but are not limited to, tissue plasminogen activator (t-PA), interferon, interleukin, growth hormone, histocompatibility and viral envelope glycoprotein signal segments.

Nucleic acid molecules of the present invention can be operatively linked to expression vectors containing regulatory sequences such as promoters, operators, repressors, enhancers, termination sequences, origins of replication, and other regulatory sequences that are compatible with the recombinant cell and that control the expression of nucleic acid molecules of the present invention. In particular, recombinant molecules of the present invention include transcription control sequences. Transcription control sequences are sequences which control the initiation, elongation, and termination of transcription. Particularly important transcription control sequences are those which control transcription initiation, such as promoter, enhancer, operator and repressor sequences. Suitable transcription control sequences include any transcription control sequence that can function in at least one of the recombinant cells of the present invention. A variety of such transcription control sequences are known to those skilled in the art. Preferred transcription control sequences include those which function in bacterial, yeast, helminth or other parasite, insect and mammalian cells, such as, but not limited to, tac, lac, trp, trc, oxy-pro, omp/lpp, rrnB, bacteriophage lambda ($\lambda$) (such as $\lambda p_L$ and $\lambda p_R$ and fusions that include such promoters), bacteriophage T7, T7lac, bacteriophage T3, bacteriophage SP6, bacteriophage SP01, metallothionein, alpha mating factor, Pichia alcohol oxidase, alphavirus subgenomic promoters (such as Sindbis virus subgenomic promoters), baculovirus, *Heliothis zea* insect virus, vaccinia virus, herpesvirus, poxvirus, adenovirus, simian virus 40, retrovirus actin, retroviral long terminal repeat, Rous sarcoma virus, heat shock, phosphate and nitrate transcription control sequences as well as other sequences capable of controlling gene expression in prokaryotic or eukaryotic cells. Additional suitable transcription control sequences include tissue-specific promoters and enhancers as well as lymphokine-inducible promoters (e.g., promoters inducible by interferons or interleukins). Transcription control sequences of the present invention can also include naturally occurring transcription control sequences naturally associated with a parasitic helminth, such as a *D. immitis*, molecule prior to isolation.

A recombinant molecule of the present invention is a molecule that can include at least one of any nucleic acid molecule heretofore described operatively linked to at least one of any transcription control sequence capable of effectively regulating expression of the nucleic acid molecule(s) in the cell to be transformed, examples of which are disclosed herein. Particularly preferred recombinant molecules include p$\beta$gal-nDiMPA1$_{1299}$, p$\beta$gal-nDiMPA2$_{2126}$, ptrcHis-nDiMPA2$_{804}$, P$\lambda$P$_R$His-nDiMPA2$_{804}$, pBBIII-nDiMPA2$_{2126}$ and ptrcHis-nDiCP$_{142}$. Details regarding the production of such recombinant molecules is disclosed herein.

A recombinant cell of the present invention includes any cell transformed with at least one of any nucleic acid molecule of the present invention. A preferred recombinant cell is a cell transformed with a nucleic acid molecule that includes at least a portion of a parasite astacin metalloendopeptidase nucleic acid molecule, such as nDiMPA1$_{689}$, nDiMPA1$_{1299}$, nDiMPA2$_{2126}$, nDiMPA2$_{804}$, nDiMPA2$_{271}$ or BvMPA2 and/or at least a portion of a filariid cysteine protease nucleic acid molecule, such as a nucleic acid molecule including nDiCP$_{143}$ or nDiCP$_{142}$. Particularly preferred recombinant cells include *E. coli*:p$\beta$gal-nDiMPA1$_{1299}$, *E. coli*:p$\beta$gal-nDiMPA2$_{2126}$, *E. coli*:ptrcHis-nDiMPA2$_{804}$, *E. coli*:p$\lambda$PRHis-nDiMPA2$_{804}$, *S. frugiperda*:pBBIII-nDiMPA2$_{2126}$ and *E. coli*:ptrcHis-nDiCP$_{142}$. Details regarding the production of these recombinant cells is disclosed herein.

Recombinant cells of the present invention can also be co-transformed with one or more recombinant molecules including nucleic acid molecules encoding one or more proteins of the present invention (e.g., parasite astacin metalloendopeptidase proteins and/or filariid cysteine protease proteins) and one or more other proteins useful in the production of multivalent vaccines which can include one or more protective compounds.

It may be appreciated by one skilled in the art that use of recombinant DNA technologies can improve expression of transformed nucleic acid molecules by manipulating, for example, the number of copies of the nucleic acid molecules within a host cell, the efficiency with which those nucleic acid molecules are transcribed, the efficiency with which the resultant transcripts are translated, and the efficiency of post-translational modifications. Recombinant techniques useful for increasing the expression of nucleic acid molecules of the present invention include, but are not limited to, operatively linking nucleic acid molecules to high-copy number plasmids, integration of the nucleic acid molecules into one or more host cell chromosomes, addition of vector stability sequences to plasmids, substitutions or modifications of transcription control signals (e.g., promoters, operators, enhancers), substitutions or modifications of translational control signals (e.g., ribosome binding sites, Shine-Dalgarno sequences), modification of nucleic acid molecules of the present invention to correspond to the codon usage of the host cell, deletion of sequences that destabilize transcripts, and use of control signals that temporally separate recombinant cell growth from recombinant enzyme production during fermentation. The activity of an expressed recombinant protein of the present invention may be improved by fragmenting, modifying, or derivatizing nucleic acid molecules encoding such a protein.

In accordance with the present invention, recombinant cells of the present invention can be used to produce one or more proteins of the present invention by culturing such cells under conditions effective to produce such a protein, and recovering the protein. Effective conditions to produce a protein include, but are not limited to, appropriate media, bioreactor, temperature, pH and oxygen conditions that permit protein production. An appropriate medium refers to any medium in which a cell of the present invention, when cultured, is capable of producing a parasite protein, including a *D. immitis* protein, of the present invention. An effective medium is typically an aqueous medium comprising assimilable carbohydrate, nitrogen and phosphate sources, as well as appropriate salts, minerals, metals and other nutrients, such as vitamins. The medium may comprise complex nutrients or may be a defined minimal medium. Cells of the present invention can be cultured in conventional fermentation bioreactors, which include, but are not limited to, batch, fed-batch, cell recycle, and continuous fermentors. Culturing can also be conducted in shake flasks, test tubes, microtiter dishes, and petri plates. Culturing is carried out at a temperature, pH and oxygen content appropriate for the recombinant cell. Such culturing conditions are well within the expertise of one of ordinary skill in the art. Examples of suitable conditions are included in the Examples section.

Depending on the vector and host system used for production, resultant proteins of the present invention may either remain within the recombinant cell; be secreted into the fermentation medium; be secreted into a space between two cellular membranes, such as the periplasmic space in *E. coli*; or be retained on the outer surface of a cell or viral membrane. The phrase "recovering the protein" refers simply to collecting the whole fermentation medium containing the protein and need not imply additional steps of separation or purification. Proteins of the present invention can be purified using a variety of standard protein purification techniques, such as, but not limited to, affinity chromatography, ion exchange chromatography, filtration, electrophoresis, hydrophobic interaction chromatography, gel filtration chromatography, reverse phase chromatography, concanavalin A chromatography, chromatofocusing and differential solubilization. Proteins of the present invention are preferably retrieved in "substantially pure" form. As used herein, "substantially pure" refers to a purity that allows for the effective use of the protein as a therapeutic composition or diagnostic. A vaccine for animals, for example, should exhibit no substantial toxicity and should be capable of stimulating the production of antibodies in a vaccinated animal.

The present invention also includes isolated antibodies capable of selectively binding to a protein of the present invention or to a mimetope thereof. Antibodies capable of selectively binding to a parasite astacin metalloendopeptidase protein of the present invention are referred to as anti-parasite astacin metalloendopeptidase antibodies. A particularly preferred antibody of this embodiment is an anti-*D. immitis* astacin metalloendopeptidase antibody. Antibodies capable of selectively binding to a filariid cysteine protease protein of the present invention are referred to as anti-filariid cysteine protease antibodies. A particularly preferred antibody of this embodiment is an anti-*D. immitis* cysteine protease antibody. Isolated antibodies are antibodies that have been removed from their natural milieu. The term "isolated" does not refer to the state of purity of such antibodies. As such, isolated antibodies can include anti-sera containing such antibodies, or antibodies that have been purified to varying degrees. As used herein, the term "selectively binds to" refers to the ability of such antibodies to preferentially bind to specified proteins and mimetopes thereof of the present invention. Binding can be measured using a variety of methods known to those skilled in the art including immunoblot assays, immunoprecipitation assays, radioimmunoassays, enzyme immunoassays (e.g., ELISA), immunofluorescent antibody assays and immunoelectron microscopy; see, for example, Sambrook et al., ibid.

Antibodies of the present invention can be either polyclonal or monoclonal antibodies. Antibodies of the present invention include functional equivalents such as antibody fragments and genetically-engineered antibodies, including single chain antibodies, that are capable of selectively binding to at least one of the epitopes of the protein or mimetope used to obtain the antibodies. Preferred antibodies are raised in response to proteins, or mimetopes thereof, that are encoded, at least in part, by a nucleic acid molecule of the present invention.

A preferred method to produce antibodies of the present invention includes (a) administering to an animal an effective amount of a protein or mimetope thereof of the present invention to produce the antibodies and (b) recovering the antibodies. Antibodies raised against defined proteins or mimetopes can be advantageous because such antibodies are not substantially contaminated with antibodies against other substances that might otherwise cause interference in a diagnostic assay or side effects if used in a therapeutic composition.

Antibodies of the present invention have a variety of potential uses that are within the scope of the present invention. For example, such antibodies can be used (a) as vaccines to passively immunize an animal in order to protect the animal from parasites susceptible to treatment by such antibodies, (b) as reagents in assays to detect infection by such parasites and/or (c) as tools to recover desired proteins of the present invention from a mixture of proteins and other contaminants.

Furthermore, antibodies of the present invention can be used to target cytotoxic agents to parasites of the present invention in order to directly kill such parasites. Targeting can be accomplished by conjugating (i.e., stably joining) such antibodies to the cytotoxic agents using techniques known to those skilled in the art. Suitable cytotoxic agents include, but are not limited to: double-chain toxins (i.e., toxins having A and B chains), such as diphtheria toxin, ricin toxin, *Pseudomonas exotoxin*, modeccin toxin, abrin toxin, and shiga toxin; single-chain toxins, such as pokeweed antiviral protein, α-amanitin, and ribosome inhibiting proteins; and chemical toxins, such as melphalan, methotrexate, nitrogen mustard, doxorubicin and daunomycin. Preferred double-chain toxins are modified to include the toxic domain and translocation domain of the toxin but lack the toxin's intrinsic cell binding domain.

One embodiment of the present invention is a therapeutic composition that, when administered to an animal in an effective manner, is capable of protecting that animal from disease caused by a parasite that is susceptible to at least one of the following treatments: immunization with an isolated parasite astacin metalloendopeptidase of the present invention, immunization with an isolated filariid cysteine protease of the present invention, administration of an inhibitor of astacin metalloendopeptidase activity or administration of an inhibitor of cysteine protease activity. As used herein, a parasite that is susceptible to such a treatment is a parasite that, if such treatment is administered to an animal in an effective manner, shows substantially reduced ability to cause disease in the animal. It is to be understood that such parasite can be susceptible to treatments other than just those listed immediately above. Such treatments can include, but are not limited to, additional treatments, or therapeutic compositions, disclosed herein.

Therapeutic compositions of the present invention include at least one of the following protective compounds: (a) an isolated parasite astacin metalloendopeptidase protein or a mimetope thereof; (b) an isolated parasite nucleic acid molecule capable of hybridizing under stringent conditions with a D. immitis astacin metalloendopeptidase gene; (c) an anti-parasite astacin metalloendopeptidase antibody; (d) an inhibitor of astacin metalloendopeptidase activity identified by its ability to inhibit parasite astacin metalloendopeptidase activity; (e) an isolated filariid nematode cysteine protease protein or a mimetope thereof; (f) an isolated filariid nematode nucleic acid molecule capable of hybridizing under stringent conditions with a D. immitis cysteine protease gene; (g) an anti-filariid nematode cysteine protease antibody; and (h) an inhibitor of cysteine protease activity identified by its ability to inhibit filariid nematode cysteine protease activity. As used herein, a protective compound refers to a compound that, when administered to an animal in an effective manner, is able to treat, ameliorate, and/or prevent disease caused by a parasite of the present invention. Preferred parasites to target are heretofore disclosed. Examples of proteins, nucleic acid molecules and antibodies of the present invention are disclosed herein. Astacin metalloendopeptidase inhibitors and cysteine protease inhibitors of the present invention are described in more detail below.

The present invention also includes a therapeutic composition comprising at least one astacin parasite metalloendopeptidase-based or filariid nematode cysteine protease-based protective compound of the present invention in combination with at least one additional compound protective against one or more infectious agents. Examples of such compounds and infectious agents are heretofore disclosed.

Therapeutic compositions of the present invention can be administered to any animal susceptible to such therapy, preferably to mammals, and more preferably to dogs, cats, humans, ferrets, horses, cattle, sheep and other pets and/or economic food animals. Preferred animals to protect include dogs, cats, humans and ferrets, with dogs and cats being particularly preferred.

In one embodiment, a therapeutic composition of the present invention can be administered to the vector in which the parasite develops from a microfilaria into L3, such as to a mosquito in order to prevent the spread of heartworm. Such administration could be orally or by developing transgenic vectors capable of producing at least one therapeutic composition of the present invention. In another embodiment, a vector, such as a mosquito, can ingest therapeutic compositions present in the blood of a host that has been administered a therapeutic composition of the present invention.

Therapeutic compositions of the present invention can be formulated in an excipient that the animal to be treated can tolerate. Examples of such excipients include water, saline, Ringer's solution, dextrose solution, Hank's solution, and other aqueous physiologically balanced salt solutions. Nonaqueous vehicles, such as fixed oils, sesame oil, ethyl oleate, or triglycerides may also be used. Other useful formulations include suspensions containing viscosity enhancing agents, such as sodium carboxymethylcellulose, sorbitol, or dextran. Excipients can also contain minor amounts of additives, such as substances that enhance isotonicity and chemical stability. Examples of buffers include phosphate buffer, bicarbonate buffer and Tris buffer, while examples of preservatives include thimerosal, m- or o-cresol, formalin and benzyl alcohol. Standard formulations can either be liquid injectables or solids which can be taken up in a suitable liquid as a suspension or solution for injection. Thus, in a non-liquid formulation, the excipient can comprise dextrose, human serum albumin, preservatives, etc., to which sterile water or saline can be added prior to administration.

In one embodiment of the present invention, the therapeutic composition can also include an immunopotentiator, such as an adjuvant or a carrier. Adjuvants are typically substances that generally enhance the immune response of an animal to a specific antigen. Suitable adjuvants include, but are not limited to, Freund's adjuvant; other bacterial cell wall components; aluminum-based salts; calcium-based salts; silica; polynucleotides; toxoids; serum proteins; viral coat proteins; other bacterial-derived preparations; gamma interferon; block copolymer adjuvants, such as Hunter's Titermax adjuvant (Vaxcel™, Inc. Norcross, Ga.); Ribi adjuvants (available from Ribi ImmunoChem Research, Inc., Hamilton, Mont.); and saponins and their derivatives, such as Quil A (available from Superfos Biosector A/S, Denmark). Carriers are typically compounds that increase the half-life of a therapeutic composition in the treated animal. Suitable carriers include, but are not limited to, polymeric controlled release formulations, biodegradable implants, liposomes, bacteria, viruses, oils, esters, and glycols.

In order to protect an animal from disease caused by a parasite of the present invention, a therapeutic composition of the present invention is administered to the animal in an effective manner such that the composition is capable of protecting that animal from a disease caused by a parasite. For example, an isolated protein or mimetope thereof, when administered to an animal in an effective manner, is able to elicit (i.e., stimulate) an immune response, preferably including both a humoral and cellular response, that is sufficient to protect the animal from the disease. Similarly, an antibody of the present invention, when administered to an animal in an effective manner, is administered in an amount so as to be present in the animal at a titer that is sufficient to protect the animal from the disease, at least temporarily. Oligonucleotide nucleic acid molecules of the present invention can also be administered in an effective manner, thereby reducing expression of astacin metalloendopeptidase or cysteine protease proteins in order to interfere with development of parasites targeted in accordance with the present invention.

Therapeutic compositions of the present invention can be administered to animals prior to infection in order to prevent infection and/or can be administered to animals after infection in order to treat disease caused by the parasite. For example, proteins, mimetopes thereof, and antibodies thereof can be used as immunotherapeutic agents.

Acceptable protocols to administer therapeutic compositions in an effective manner include individual dose size, number of doses, frequency of dose administration, and mode of administration. Determination of such protocols can be accomplished by those skilled in the art. A suitable single dose is a dose that is capable of protecting an animal from disease when administered one or more times over a suitable time period. For example, a preferred single dose of a protein, mimetope or antibody therapeutic composition is from about 1 microgram (µg) to about 10 milligrams (mg) of the therapeutic composition per kilogram body weight of the animal. Booster vaccinations can be administered from about 2 weeks to several years after the original administration. Booster vaccinations preferably are administered when the immune response of the animal becomes insufficient to protect the animal from disease. A preferred administration schedule is one in which from about 10 µg to about 1 mg of the vaccine per kg body weight of the animal is administered from about one to about two times over a time period of from about 2 weeks to about 12 months. Modes of administration can include, but are not limited to, subcutaneous, intradermal, intravenous, nasal, oral, transdermal and intramuscular routes.

According to one embodiment, a nucleic acid molecule of the present invention can be administered to an animal in a fashion to enable expression of that nucleic acid molecule into a protective protein or protective RNA (e.g., antisense RNA, ribozyme or RNA drug) in the animal to be protected from disease. Nucleic acid molecules can be delivered to an animal in a variety of methods including, but not limited to, (a)direct injection (e.g., as "naked" DNA or RNA molecules, such as is taught, for example in Wolff et al., 1990, *Science* 247, 1465–1468) or (b) packaged as a recombinant virus particle vaccine or as a recombinant cell vaccine (i.e., delivered to a cell by a vehicle selected from the group consisting of a recombinant virus particle vaccine and a recombinant cell vaccine).

A recombinant virus particle vaccine of the present invention includes a recombinant molecule of the present invention that is packaged in a viral coat and that can be expressed in an animal after administration. Preferably, the recombinant molecule is packaging-deficient. A number of recombinant virus particles can be used, including, but not limited to, those based on alphaviruses, poxviruses, adenoviruses, herpesviruses, and retroviruses. Preferred recombinant particle viruses are those based on alphaviruses (such as Sindbis virus), herpesviruses and poxviruses. Methods to produce and use recombinant virus particle vaccines are disclosed in U.S. patent application Ser. No. 08/015,414, filed Feb. 8, 1993, entitled "Recombinant Virus Particle Vaccines", which is incorporated by reference herein in its entirety.

When administered to an animal, a recombinant virus particle vaccine of the present invention infects cells within the immunized animal and directs the production of a protective protein or RNA nucleic acid molecule that is capable of protecting the animal from disease caused by a parasite of the present invention. For example, a recombinant virus particle comprising a *D. immitis* astacin metalloendopeptidase nucleic acid molecule and/or a *D. immitis* cysteine protease nucleic acid molecule of the present invention is administered according to a protocol that results in the animal producing a sufficient immune response to protect itself from heartworm. A preferred single dose of a recombinant virus particle vaccine of the present invention is from about $1 \times 10^4$ to about $1 \times 10^7$ virus plaque forming units (pfu) per kilogram body weight of the animal. Administration protocols are similar to those described herein for protein-based vaccines.

A recombinant cell vaccine of the present invention includes recombinant cells of the present invention that express at least one protein of the present invention. Preferred recombinant cells include Salmonella, *E. coli*, Mycobacterium, *S. frugiperda*, baby hamster kidney, myoblast G8, COS, MDCK and CRFK recombinant cells, with Salmonella recombinant cells being more preferred. Such recombinant cells can be administered in a variety of ways but have the advantage that they can be administered orally, preferably at doses ranging from about $10^8$ to about $10^{12}$ bacteria per kilogram body weight. Administration protocols are similar to those described herein for protein-based vaccines. Recombinant cell vaccines can comprise whole cells or cell lysates.

In common with most other enteric pathogens, Salmonella strains normally enter the host orally. Once in the intestine, they interact with the mucosal surface, normally to establish an invasive infection. Most Salmonella infections are controlled at the epithelial surface, causing the typical Salmonella-induced gastroenteritis. Some strains of Salmonella, including *S. typhi* and some *S. typhimurium* isolates, have evolved the ability to penetrate deeper into the host, causing a disseminated systemic infection. It appears such strains have the capacity to resist the killing actions of macrophages and other immune cells. *S. typhi* can exist for long periods as a facultative intracellular parasite. Some of the live vaccine strains can also persist for long periods in the mononuclear phagocyte system. Hosts infected in such a manner develop, in addition to a mucosal immune response, systemic cellular and serum antibody responses to the Salmonella. Thus, invading Salmonella, whether virulent or attenuated, can stimulate strong immune responses, unlike many other enteric pathogens which only set up local, noninvasive gut infections. The potent immunogenicity of live Salmonella makes them attractive candidates for carrying nucleic acid molecules of the present invention, and the proteins they encode, to the immune system.

A preferred recombinant cell-based vaccine is one in which the cell is attenuated. *Salmonella typhimurium* strains, for example, can be attenuated by introducing mutations into genes critical for in vivo growth and survival. For example, genes encoding cyclic adenosine monophosphate (cAMP) receptor protein or adenylate cyclase are deleted to produce avirulent, vaccine strains. Such strains can deliver antigens to lymphoid tissue in the gut but demonstrate reduced capacity to invade the spleen and mesenteric lymph nodes. These strains are still capable of stimulating both humoral and cellular immunity in mammalian hosts.

Recombinant cell vaccines can be used to introduce proteins of the present invention into the immune systems of animals. For example, recombinant molecules comprising nucleic acid molecules of the present invention operatively linked to expression vectors that function in Salmonella can be transformed into Salmonella host cells. The resultant recombinant cells are then introduced into the animal to be protected. Preferred Salmonella host cells are those for which survival depends on their ability to maintain the recombinant molecule (i.e., a balanced-lethal host-vector system). An example of such a preferred host/recombinant molecule combination is a Salmonella strain (e.g., UK-1 $_\chi$3987 or SR-11 $_\chi$4072) which is unable to produce aspartate β-semialdehyde dehydrogenase in combination with a recombinant molecule also capable of encoding the enzyme. Aspartate β-semialdehyde dehydrogenase, encoded by the asd gene, is an important enzyme in the pathway to produce diaminopimelic acid (DAP). DAP is an essential component of the peptidoglycan of the cell wall of Gram-negative bacteria, such as Salmonella, and, as such, is necessary for survival of the cell. Thus, Salmonella lacking a functional asd gene can only survive if they maintain a recombinant molecule that is also capable of expressing a functional asd gene.

In one embodiment, a nucleic acid molecule of the present invention is inserted into expression vector pTECH-1 (available from Medeva, London, U.K.) and the resulting recombinant molecule is transfected into a Salmonella strain, such as BRD 509 (available from Medeva), to form a recombinant cell. Such recombinant cells can be used to produce the corresponding encoded protein or can be used as recombinant cell vaccines.

One preferred embodiment of the present invention is the use of nucleic acid molecules and proteins of the present invention, and particularly $D.$ $immitis$ nucleic acid molecules and proteins of the present invention, to protect an animal from heartworm. Preferred therapeutic compositions are those that are able to inhibit at least one step in the portion of the parasite's development cycle that includes L3 larvae, third molt, L4 larvae, fourth molt and immature adult prior to entering the circulatory system. In dogs, this portion of the development cycle is about 70 days. As such, preferred therapeutic compositions include $D.$ $immitis$ astacin metalloendopeptidase-based and $D.$ $immitis$ cysteine protease-based therapeutic compounds of the present invention. Such compositions are administered to animals in a manner effective to protect the animals from heartworm. Additional protection may be obtained by administering additional protective compounds, including other $D.$ $immitis$ proteins, nucleic acid molecules and antibodies as heretofore disclosed.

One embodiment of the present invention is the use of enzymatically active parasite astacin metalloendopeptidase and/or filariid nematode cysteine protease proteins of the present invention to identify inhibitors of such enzyme activity. While not being bound by theory, it is believed that parasites use such proteases in a number of ways, including, but not limited to, to effect embryonic and larval development, to effect molting and to effect tissue migration both as larvae and adults. Such proteases are capable of degrading cutaneous connective tissue macromolecules as well as other proteinaceous material to facilitate such functions. It is also of interest that astacin metalloendopeptidases identified in sea urchins, Drosophila and Xenopus have been linked with development and maturation of the respectively organisms. As such, inhibitors of astacin metalloendopeptidase and/or cysteine protease activity could be particularly beneficial in disrupting embryonic and/or larval development or molting by parasites in general and tissue migration by those parasites capable of such migration. Use of parasite enzymes to develop such inhibitors is also advantageous because inhibitors can be identified that are highly selective for the parasite without causing undue side effects to the animal being treated.

One therapeutic composition of the present invention includes an inhibitor of parasite astacin metalloendopeptidase activity, i.e., a compound capable of substantially interfering with the function of a parasite astacin metalloendopeptidase susceptible to inhibition by an inhibitor of $D.$ $immitis$ astacin metalloendopeptidase activity. An inhibitor of astacin metalloendopeptidase can be identified using enzymatically active parasite and preferably $D.$ $immitis,$ astacin metalloendopeptidase proteins of the present invention.

One embodiment of the present invention is a method to identify a compound capable of inhibiting astacin metalloendopeptidase activity of a parasite. Such a method includes the steps of (a) contacting (e.g., combining, mixing) an isolated parasite, preferably $D.$ $immitis,$ astacin metalloendopeptidase protein with a putative inhibitory compound under conditions in which, in the absence of the compound, the protein has astacin metalloendopeptidase activity, and (b) determining if the putative inhibitory compound inhibits the astacin metalloendopeptidase activity. Putative inhibitory compounds to screen include organic molecules, antibodies (including functional equivalents thereof) and substrate analogs. Methods to determine astacin metalloendopeptidase activity are known to those skilled in the art; see, for example, Gomis-Ruth, et al. ibid., and referenced cited therein.

The present invention also includes a test kit to identify a compound capable of inhibiting astacin metalloendopeptidase activity of a parasite. Such a test kit includes an isolated parasite, preferably $D.$ $immitis,$ astacin metalloendopeptidase protein having astacin metalloendopeptidase activity and a means for determining the extent of inhibition of astacin metalloendopeptidase activity in the presence of (i.e., effected by) a putative inhibitory compound.

Astacin metalloendopeptidase inhibitors isolated by such a method, and/or test kit, can be used to inhibit any astacin metalloendopeptidase that is susceptible to such an inhibitor. Preferred astacin metalloendopeptidase enzymes to inhibit are those produced by parasites. A particularly preferred astacin metalloendopeptidase inhibitor of the present invention is capable of protecting an animal from heartworm. It is also within the scope of the present invention to use inhibitors of the present invention to target astacin metalloendopeptidase-related disorders in animals. Therapeutic compositions comprising astacin metalloendopeptidase inhibitory compounds of the present invention can be administered to animals in an effective manner to protect animals from disease caused by the targeted astacin metalloendopeptidase enzymes, and preferably to protect animals from heartworm. Effective amounts and dosing regimens can be determined using techniques known to those skilled in the art.

Another therapeutic composition of the present invention includes an inhibitor of parasite cysteine protease activity, i.e., a compound capable of substantially interfering with the function of a parasite cysteine protease susceptible to inhibition by an inhibitor of filariid nematode cysteine protease activity. A cysteine protease inhibitor can be identified using enzymatically active filariid nematode, and preferably $D.$ $immitis,$ cysteine protease proteins of the present invention.

One embodiment of the present invention is a method to identify a compound capable of inhibiting cysteine protease activity of a parasite. Such a method includes the steps of (a) contacting (e.g., combining, mixing) an isolated filariid nematode, preferably $D.$ $immitis,$ cysteine protease protein with a putative inhibitory compound under conditions in which, in the absence of the compound, the protein has cysteine protease activity, and (b) determining if the putative inhibitory compound inhibits the cysteine protease activity. Putative inhibitory compounds to screen include organic molecules, antibodies (including functional equivalents thereof) and substrate analogs. Methods to determine cysteine protease activity are known to those skilled in the art, as heretofore disclosed.

The present invention also includes a test kit to identify a compound capable of inhibiting cysteine protease activity of a parasite. Such a test kit includes an isolated filariid nematode, preferably $D.$ $immitis,$ cysteine protease protein having cysteine protease activity and a means for determining the extent of inhibition of cysteine protease activity in the presence of (i.e., effected by) a putative inhibitory compound.

Inhibitors isolated by such a method, and/or test kit, can be used to inhibit any cysteine protease that is susceptible to such an inhibitor. Preferred cysteine protease enzymes to inhibit are those produced by parasites. A particularly preferred cysteine protease inhibitor of the present invention is capable of protecting an animal from heartworm. It is also within the scope of the present invention to use inhibitors of the present invention to target cysteine protease-related disorders in animals. Therapeutic compositions comprising cysteine protease-inhibitory compounds of the present invention can be administered to animals in an effective manner to protect animals from disease caused by the targeted cysteine protease. Effective amounts and dosing regimens can be determined using techniques known to those skilled in the art.

The efficacy of a therapeutic composition of the present invention to protect an animal from disease caused by a parasite can be tested in a variety of ways including, but not limited to, detection of protective antibodies (using, for example, proteins or mimetopes of the present invention), detection of cellular immunity within the treated animal, or challenge of the treated animal with the parasite to determine whether the treated animal is resistant to disease. Such techniques are known to those skilled in the art.

In accordance with the present invention, the inventors have shown that protease inhibitors can inhibit parasite larval development. For example, bestatin and phosphoramidon have been shown to inhibit molting of D. immitis larvae, as described in more detail in the Examples.

Another embodiment of the present invention includes the isolation of proteases, including metalloproteases and cysteine proteases from parasitic larval excretory/secretory (ES) products. Using a modified version of the protocol first described in U.S. patent application Ser. No. 08/153,554, ibid., the inventors have, for example, isolated a fraction comprising a protein of approximately 60 kD (as determined by Tris-glycine sodium dodecyl sulfate polyacrylamide gel electrophoresis (SDS-PAGE) that has metalloprotease activity as determined by the protein's ability to cleave H-Phe-AMC. When submitted to size-exclusion chromatography, the active fraction elutes with bovine serum albumin, indicating an 20 approximate molecular weight of from about 62 to about 66 kD. The modified protocol, which is described in more detail in the Examples, includes submitting parasitic, preferably D. immitis, larval ES, to anion exchange chromatography, followed by size exclusion chromatography and isoelectric focussing. The active fraction has a pI of about 6.8.

In another embodiment, the inventors have identified at least one parasite metalloprotease from the ES that is capable of degrading collagen. For example, electrophoresis of D. immitis larval ES through a gelatin-based matrix leads to isolated active fractions that migrate with apparent molecular weights of about 60, 95 and at least about 200 kD. The proteolytic activity of such fractions is essentially completely inhibited by EDTA.

It is also within the scope of the present invention to use isolated proteins, mimetopes, nucleic acid molecules and antibodies of the present invention as diagnostic reagents to detect infection by parasites. Such diagnostic reagents can be supplemented with additional compounds that can detect other phases of the parasite's life cycle.

The following examples are provided for the purposes of illustration and are not intended to limit the scope of the present invention.

EXAMPLES

The following examples include a number of recombinant DNA and protein chemistry techniques which are known to those skilled in the art; see, for example, Sambrook et al., ibid.

Example 1

This Example discloses the cloning and sequencing of two parasite astacin metalloendopeptidase nucleic acid molecules of the present invention. This Example also discloses the production of a recombinant molecule and recombinant cell of the present invention.

A D. immitis third stage larvae cDNA expression library was prepared in the following manner. Total RNA was extracted from D. immitis third stage larvae (L3) using an acid-guanidinium-phenol-chloroform method similar to that described by Chomczynski and Sacchi, 1987, Anal. Biochem. 162, p. 156–159. Approximately 230,000 L3 were used in the RNA preparation. Poly A+ selected RNA was separated from total RNA by oligo-dT cellulose chromatography using Oligo dT cellulose from Collaborative Research Inc., Waltham, Mass., according to the method recommended by the manufacturer.

The expression library was constructed by inserting the L3 poly A+ RNA into the expression vector lambda (λ) Uni-ZAP™ XR (available from Stratagene Cloning Systems, La Jolla, Calif.) using Stratagene's ZAP-cDNA Synthesis Kit® protocol and about 6–7 µg of L3 poly A+ RNA. The resultant library was amplified to a titer of about $4.88 \times 10^9$ pfu/ml with about 96% recombinants. Ten minilibraries were generated by one further round of amplification of randomly selected aliquots of the original L3 cDNA amplified library. These minilibrary phage were collected in phage dilution buffer (e.g., 10 mM Tris-HCl, pH 7.5, 10 mM magnesium sulfate) and stored at 4° C.

A D. immitis astacin metalloendopeptidase nucleic acid molecule of about 689 nucleotides, representing a partial D. immitis astacin metalloendopeptidase gene and denoted nDiMPA1$_{689}$, was PCR amplified from D. immitis L3 cDNA expression minilibraries using the following two primers: a 4-fold degenerate primer having SEQ ID NO:14, namely 5'ACWCATGAAATIGSICAT 3' (denoted MP1; W can be A or T; S can be C or G; I is inosine) and an antisense oligonucleotide having SEQ ID NO:15, namely 5'AATAC-GACTCACTATAG 3' (denoted T7). Primer MP1 was designed from published sequences of the metalloprotease conserved zinc binding domain. Primer T7 is complementary to the pBluescript® vector (available from Stratagene).

A nucleic acid molecule amplified from minilibrary number 10, which was denoted nDiMPA1$_{689}$, was gel-purified, electroeluted and cloned into the cloning vector pCRII (available from Invitrogen, San Diego, Calif.) following manufacturer's instructions, thereby forming recombinant vector pCRII-nDiMPA1$_{689}$. The nucleotide sequence of nDiMPA1$_{689}$ was determined and found to include nucleotides spanning from about nucleotide position 610 through the 3' end of SEQ ID NO:1, the production of which is described in more detail below.

The L3 cDNA minilibrary number 10 was screened with the radiolabeled MP1 oligonucleotide as a probe, using stringent (i.e., standard) hybridization conditions as described in Sambrook et al., ibid. Plaques which hybridized to the probe were rescreened and plaque-purified. The plaque-purified clone including *D. immitis* nucleic acid molecule nDiMPA1$_{1299}$ was converted into a double stranded recombinant molecule, herein denoted as pβgal-nDiMPA1$_{1299}$, using R408 helper phage and XL1-Blue *E. coli* according to the in vivo excision protocol described in the Stratagene ZAP-cDNA Synthesis Kit®. Double-stranded plasmid DNA was prepared using an alkaline lysis protocol, such as that described in Sambrook et al., ibid. Recombinant molecule pβgal-nDiMPA1$_{1299}$ was transformed into *E. coli* to form recombinant cell *E. coli*:pβgal-nDiMPA1$_{1299}$.

Recombinant molecule pβgal-nDiMPA1$_{1299}$ was submitted to nucleic acid sequencing using the Sanger dideoxy chain termination method, as described in Sambrook et al., ibid. An about 1299 nucleotide consensus sequence of nucleic acid molecule nDiMPA1$_{1299}$ was determined and is presented as SEQ ID NO:1. SEQ ID NO:1 apparently encodes three overlapping open reading frames. The first open reading frame, denoted PDiMPA1$_{ORF1}$, is about 191 amino acids (presented in SEQ ID NO:3) and encompasses about nucleotide number 18–590 of SEQ ID NO:1. The second open reading frame, denoted PDiMPA1$_{ORF2}$, is about 141 amino acids (presented in SEQ ID NO:4) and encompasses about nucleotide number 508–930 of SEQ ID:1. Open reading frame PDiMPA1$_{ORF2}$ includes the extended zinc binding domain and hydrophilic region HEIGHTLGIFHE beginning at about amino acid 36 of SEQ ID NO:4, as well as the domain YDTGSVMHY (beginning at about amino acid position 87) that includes the tyrosine that is thought to bind to zinc at about amino acid position 95. The third open reading frame, denoted PDiMPA1$_{ORF3}$, is about 121 amino acids (presented in SEQ ID NO:5) and encompasses nucleotide number 785–1147 of SEQ ID:1.

A homology search of the non-redundant protein sequence database was performed through the National Center for Biotechnology Information using the BLAST network. This database includes +SwissProt+PIR+SPUpdate+GenPept+GPUpdate. The search, which was performed using SEQ ID NO:3, SEQ ID NO:4 and SEQ ID NO:5, showed significant homology at the amino acid level by all three open reading frames to members of the astacin family of metalloendopeptidases. Significant homology throughout all three amino acid open reading frames is also associated with a *C. elegans* R151.5 gene product, Genbank accession number U00036.

It was apparent from the pbluescript vector sequences at and near the 5' end of nucleic acid molecule nDiMPA1$_{1299}$ that two cDNA fragments had ligated to each other via their 5' ends to form that nucleic acid molecule. A comparison of the nucleotide sequence of SEQ ID NO:1 to that of SEQ ID NO:2 (the apparent nucleotide sequence of independently-isolated astacin metalloendopeptidase nucleic acid molecule nDiMPA2$_{2126}$ described in Example 2) as well as to nucleotide sequences of other members the astacin family of metalloendopeptidases, showed that nucleotide number 56 of SEQ ID NO:1 corresponds to the first nucleotide on the 5' end of nDiMPA2$_{2126}$ suggesting that nucleotide number 56 represents the junction of the two different cDNA sequences in nDiMPA1$_{1299}$. Therefore, nucleotides 1 through 55 of nDiMPA1$_{1299}$ most likely represent a non-astacin related CDNA sequence which ligated to the 5' end of the astacin metalloendopeptidase cDNA fragment prior to cloning. Astacin homology at the amino acid level can be found starting with amino acid number 125 of the first open reading frame of nDiMPA1$_{1299}$, namely PDiMPA1$_{ORF1}$.

Example 2

This Example discloses the cloning and sequencing of an additional parasite astacin metalloendopeptidase nucleic acid molecule of the present invention. This Example also discloses the production of a recombinant molecule and recombinant cell of the present invention.

Due to the unusual sequences on the 5' end of astacin metalloendopeptidase nucleic acid molecule nDiMPA1$_{1299}$, a second astacin metalloendopeptidase nucleic acid molecule, denoted nDiMPA2$_{2126}$, was isolated from the L3 cDNA expression library described in Example 1, as follows.

A *D. immitis* astacin metalloendopeptidase nucleic acid molecule of about 271 nucleotides, denoted nDiMPA2$_{271}$, was PCR amplified from *D. immitis* L3 cDNA expression minilibrary number 9 using the following two primers: an oligonucleotide having SEQ ID NO:16, namely 5'TGGTATTATATCACATGAAATTGGTCATAC 3' (denoted ZNSEN) and an antisense oligonucleotide having SEQ ID NO:17, namely 5'CCCAATTGTGTACTGTTGAAATTTATCAC 3' (denoted MP14). Primer ZNSEN was designed from the nucleotide sequence encoding the metalloprotease conserved zinc binding domain in nDiMPA1$_{1299}$ and spans from about nucleotide 600 through about nucleotide 629 of SEQ ID NO:1. Primer MP14 is an antisense primer complementary to a region spanning from about nucleotide 842 through about nucleotide 870 of nDiMPA1$_{1299}$.

Nucleic acid molecule nDiMPA2$_{271}$ was radiolabeled and used as a probe to screen L3 cDNA minilibrary number 9. Plaques which hybridized under stringent hybridization conditions to the probe were rescreened and plaque purified. A plaque-purified clone including *D. immitis* nucleic acid molecule nDiMPA2$_{2126}$, was converted into a double-stranded recombinant molecule, herein denoted as pβgal-nDiMPA2$_{2126}$, using R408 helper phage and XL1-Blue *E. coli* according to the in vivo excision protocol described in the Stratagene ZAP-cDNA Synthesis Kit®. Double-stranded plasmid DNA was prepared using an alkaline lysis protocol, such as that described in Sambrook et al., ibid. Recombinant molecule pβgal-nDiMPA2$_{2126}$ was transformed into *E. coli* to form recombinant cell *E. coli*:pβgal-nDiMPA2$_{2126}$.

Recombinant molecule pβgal-nDiMPA2$_{2126}$ was submitted to nucleic acid sequencing using the Sanger dideoxy chain termination method, as described in Sambrook et al., ibid. An about 2126-nucleotide consensus sequence of nucleic acid molecule nDiMPA2$_{2126}$ was determined and is presented as SEQ ID NO:2. SEQ ID NO:2 apparently encodes five overlapping open reading frames. The first open reading frame, denoted PDiMPA2$_{ORF1}$, is about 178 amino acids (presented in SEQ ID NO:6) and encompasses about nucleotide numbers 2–535 of SEQ ID:2. The second open reading frame, denoted PDiMPA2$_{ORF2}$, is about 145 amino acids (presented in SEQ ID NO:7) and encompasses about nucleotide numbers 453–887 of SEQ ID:2. PDiMPA2$_{ORF2}$ includes the extended zinc binding domain, beginning at about amino acid 36 of SEQ ID NO:7 as well as the tyrosine-containing motif, beginning at about amino acid 87. The third open reading frame, denoted PDiMPA2$_{ORF3}$, is about 134 amino acids (presented in SEQ ID NO:8) and encompasses nucleotide number 730–1131 of SEQ ID:2. The fourth open reading frame, denoted PDiMPA2$_{ORF4}$, is about 154 amino acids (presented in SEQ ID NO:9) and encompasses nucleotide number 1112–1573 of SEQ ID:2. The fifth open reading frame, denoted PDiMPA$^2_{ORF5}$, is about 163 amino acids (presented in SEQ ID NO:10) and encompasses nucleotide number 1429–1917 of SEQ ID:2.

A comparison of the deduced nucleic acid sequences of nDiMPA1$_{1299}$ (SEQ ID NO:1) and nDiMPA2$_{2126}$ (SEQ ID NO:2) indicates that nDiMPA2$_{2126}$ does not contain the stretch of nucleotides from about positions 1 through 55 of nDiMPA1$_{1299}$ (as numbered in SEQ ID NO:1). As discussed above, it is believed that this stretch of nucleotides represents an unrelated cDNA clone that ligated to the 5' end of the astacin metalloendopeptidase nucleic acid molecule. The stretch of nucleotides spanning from about positions 56 through 907 of nDiMPA1$_{1299}$ (as numbered in SEQ ID NO:1) share 100% homology with the stretch of nucleotides spanning from about positions 1 through 852 of nDiMPA2$_{2126}$ (as numbered in SEQ ID NO:2). The stretch of nucleotides spanning from about positions 908 through 970 of nDiMPA1$_{1299}$ (as numbered in SEQ ID NO:1) are missing from nDiMPA2$_{2126}$. The stretch of nucleotides spanning from about positions 971 through 1133 of nDiMPA1$_{1299}$ (as numbered in SEQ ID NO:1) share 100% homology with the stretch of nucleotides spanning from about positions 853 through 1015 of nDiMPA2$_{2126}$ (as numbered in SEQ ID NO:2). Nucleic acid molecule nDiMPA2$_{2126}$ has a significantly longer 3' end than does nDiMPA1$_{1299}$.

A homology search of the non-redundant protein sequence database was performed through the National Center for Biotechnology Information using the BLAST network. This database includes +SwissProt+PIR+SPUpdate+GenPept+GPUpdate. The search, which was performed using SEQ ID NO:7, SEQ ID NO:8, SEQ ID NO:9 and SEQ ID NO:10 and SEQ ID NO:11, showed that SEQ ID NO:7, SEQ ID NO:8, SEQ ID NO:9 and SEQ ID NO:10 each shared significant homology at the amino acid level with known members of the astacin family of metalloendopeptidases. SEQ ID NO:11, in contrast did not show significant homology to a known astacin metalloendopeptidase.

A composite D. immitis ORF of the five open reading frames encoded by nDiMPA2$_{2126}$ was produced by lining up the five ORFs in relation to known astacin metalloendopeptidase sequences. The composite D. immitis ORF, which spans a region significantly larger than the 200-amino acid astacin protein, is presented in SEQ ID NO:11. A comparison between the astacin domain of SEQ ID NO:11 and crayfish astacin showed about 29% homology at the amino acid level. The astacin domain of SEQ ID NO:11 also shared about 30 percent, 31 percent, 33 percent and 33 percent homology at the amino acid level with the astacin domains of, respectively, human bone morphogenetic protein 1, mouse kidney brush border metalloendopeptidase, human intestinal brush border metalloendopeptidases and Xenopus laevis embryonic protein UVS.2.

Comparison of SEQ ID NO:11 and the C. elegans R151.5 gene product, (Genbank accession number U00036) showed an about 24% homology between the two sequences. The C. elevans gene product also includes a well-conserved extended zinc binding domain motif and tyrosine-containing motif. It is interesting that although the C. elegans R151.5 gene product was identified by Wilson et al., ibid., as an open reading frame, the authors of that publication describing a 2.2 megabase contiguous nucleotide sequence from the free-living nematode C. elegans failed to appreciate the homology between R151.5 and the family of astacin metalloendopeptidases. The present inventors are apparently the first to note such a homology and the likelihood that C. elegans encodes an astacin metalloendopeptidase.

Example 3

This Example discloses the production of a recombinant cell of the present invention and its use to produce a parasitic astacin metalloendopeptidase protein of the present invention.

Recombinant molecule ptrcHis-nDiMPA2$_{804}$, containing nucleotides from about positions 119 through 922 of nDiMPA2$_{2126}$ (as numbered in SEQ ID NO:2) operatively linked to trc transcription control sequences and to a fusion sequence encoding a poly-histidine segment comprising 6 histidines was produced in the following manner. An about 804-nucleotide DNA fragment containing nucleotides spanning from about 119 through about 922 of nDiMPA2$_{2126}$ (as numbered in SEQ ID NO:2), denoted nDiMPA2$_{804}$ was cleaved from recombinant molecule pβgal-nDiMPA2$_{2126}$, with BamHI restriction endonuclease, gel purified and subcloned into expression vector pTrcHisB (available from Invitrogen) that had been cleaved with BamHI. The resulting recombinant olecule ptrcHis-nDiMPA2$_{804}$ was transformed into E. coli to form recombinant cell E. coli:ptrcHis-nDiMPA2$_{804}$.

Recombinant cell E. coli:ptrcHis-nDiMPA2$_{804}$ is cultured in shake flasks containing an enriched bacterial growth medium containing about 0.1 mg/ml ampicillin at about 37° C. When the cells reach an OD$_{600}$ of about 0.3, expression of E. coli:ptrcHis-nDiMPA2$_{804}$ is induced by addition of about 1 mM isopropyl-β-D-thiogalactoside (IPTG), and the cells cultured for about 3 hours at about 37° C. Protein production is monitored by SDS-PAGE of recombinant cell lysates, followed by Coomassie blue staining, using standard techniques. Recombinant cell E. coli:ptrcHis-nDiMPA2$_{804}$ produces a fusion protein, denoted herein as PHIS-PDiMPA2$_{804}$, that is not produced by cells transformed with the pTrcHisB plasmid lacking a parasite nucleic acid molecule insert.

Example 4

This Example discloses the production of another recombinant cell of the present invention capable of producing a parasitic astacin metalloendopeptidase protein of the present invention.

Recombinant molecule pαP$_R$His-nDiMPA2$_{804}$, containing nucleotides from about positions 119 through 922 of nDiMPA2$_{2126}$ (as numbered in SEQ ID NO:2) operatively linked to λP$_R$ transcription control sequences and to a fusion sequence encoding a poly-histidine segment comprising 6 histidines was produced in the following manner. Nucleic acid molecule nDiMPA2$_{804}$, produced as described in Example 3, was ligated into the BamHI restriction site of the αP$_R$/T7/RSET-B expression vector. The vector, which is about 3455 base pairs (bp), contains an about 1990-bp pair PvuII to AatII fragment from pUC19 containing the ampicillin resistance gene and E. coli origin of replication; an about 1100 bp BglII to BglII DNA fragment from vector pRK248cIts (available as ATCC #33766) with a PvuII linker added to one end, containing the αP$_R$ promoter, the cI$^{857}$ α repressor gene and 22 amino acids of the cro gene regulating lytic growth; an about 55-bp BglII to XbaI segment from pGEMEX-1 (available from Promega, Madison, Wis.) which contains the T7 promoter; an about 170-bp XbaI to EcoRI segment from pRSET-B (available from Invitrogen) which contains the T7-S10 translational enhancer, the His6 fusion, the 11 amino acid S10 leader fusion, an enterokinase cleavage site and the multiple cloning site; and an about 140-bp fragment containing synthetic translational and transcription termination signals including the T$_1$ translation terminators in all three reading frames, RNA stabilization sequence from Bacillus thurengiensis crystal protein and the T$_2$ rho-independent transcription terminator from the trpA operon. The resulting recombinant molecule, denoted pαP$_R$His-nDiMPA2$_{804}$, was transformed into E. coli to form recombinant cell E. coli:pαP$_R$His-nDiMPA2$_{804}$.

Example 5

This Example describes another recombinant cell of the present invention and its use to produce a parasitic astacin metalloendopeptidase protein of the present invention.

Recombinant molecule pBBIII-nDiMPA2$_{2126}$, containing nucleic acid molecule nDiMPA2$_{2126}$ (produced as described in Example 2) operatively linked to baculovirus polyhedron transcription control sequences was produced in the following manner. In order to produce a baculovirus recombinant molecule capable of directing the production of the protein encoded by nDiMPA2$_{2126}$, recombinant molecule pβgal-nDiMPA2$_{2126}$, produced as described in Example 2, was digested with XhoI, end-filled with Klenow DNA Polymerase, digested with PstI, gel purified and referred to as BvMPA2. The baculovirus shuttle plasmid, BlueBacIII (BBIII) (available from Invitrogen) was digested with NcoI, end-filled, digested with PstI and treated with calf intestinal phosphatase. The resulting vector fragment was gel purified and ligated to BvMPA2. The resultant recombinant molecule, denoted pBBIII-nDiMPA2$_{2126}$, was verified for proper insert orientation by restriction mapping. This construct and linear *Baculogold baculovirus* DNA (Pharmingen) were cotransfected into *Spodoptera frugiperda* Sf9 host cells (donated by Colorado Bioprocessing Center, Fort Collins, Colo.). The resulting recombinant virus termed BvMPA, was cultivated for increased production of recombinant virus and to verify expression of nDiMPA2$_{2126}$ by Western blot.

Example 6

This Example describes the cloning and sequencing of a filariid nematode cysteine protease nucleic acid molecule of the present invention.

A *D. immitis* cysteine protease nucleic acid molecule of about 143 nucleotides, denoted nDiCP$_{143}$, representing a partial *D. immitis* cysteine protease gene, was PCR amplified from *D. immitis* genomic DNA that had been extracted from adult female *D.immitis* worms using standard protocols similar to that described in Sambrook et al, ibid. The two primers used in the PCR amplification reaction included a 4-fold degenerate primer having SEQ ID NO:18, namely 5' CGGGATCCTGTGGWTCATGYTGGGC 3' (denoted 25C; BamHI site in bold; W is A or T; Y is C or T) and an 8-fold degenerate antisense primer having SEQ ID No:19, namely 5'TAICCICCRTTRCAICCYTC 3' (denoted G65; R is A or G; Y is C or T; I is inosine). Both primers were designed from published sequence of cysteine proteases. Primer 25C was further refined in that *D. immitis* codon bias was incorporated into 25C to reduce the degeneracy. The inventors found such codon bias was necessary to effectively isolate *D. immitis* cysteine protease nucleic acid molecules of the present invention.

The amplified PCR fragment, namely nDiCP$_{143}$, was gel purified and cloned into the pCRII cloning vector (available from Invitrogen, San Diego, Calif.), following manufacturer's instructions. An about 143 nucleotide sequence of nDiCP$_{143}$ was determined and is presented as SEQ ID NO:12. SEQ ID NO:12 apparently encodes a protein of about 47 amino acids, which is presented as SEQ ID NO:13. The translation initiation site of the protein and the translation termination codon are not contained within this genomic clone.

A homology search of the non-redundant protein sequence database was performed through the National Center for Biotechnology Information using the BLAST network. This database includes +SwissProt+PIR+SPUpdate+GenPept+GPUpdate. The search was performed using SEQ ID NO:13 and showed significant homology to numerous cysteine proteinases. The highest scoring matches at the amino acid level include soybean probable thiol protease precursor (Genbank accession number P22895), barley cysteine proteinase EP-B 1 precursor (Genbank accession number P25249) and barley cysteine proteinase EP-B 4 precursor (Genbank accession number P25250). Parasite specific cysteine proteases having homology to SEQ ID NO:13 include cysteine proteases from *Trypanosoma brucei* (Genbank accession numbers S07051 and S12099), *Leishmania pifanoi* (Genbank accession number B48566), *L. mexicana* (Genbank accession number S25003), *T. congolense* (Genbank accession number (37048), and *Trichomonas vaginalis* (Genbank accession number X77220). SEQ ID NO:13 shared about 16 percent, about 22 percent, about 24 percent, about 35 percent, about 39 percent, about 44 percent and about 49 percent homology at the amino acid level with cysteine proteases from, respectively, *H. contortus* (a nematode), *Schistosoma mansoni* (a trematode), *C. elegans* (a nematode), *Fasciola hepatica* (a trematode), *Entamoeba histolytica* (a protozoa), *Trypanosoma cruzi* (a protozoa) and *T. brucie*. SEQ ID NO:13 also shared about 50 percent amino acid homology with human cathepsin. SEQ ID NO:13 also shared about 56 percent amino acid homology with a *Paragonimus westermani* cysteine protease reported in European Patent Application Publication No. 0524834A2, by Hamajima et al., published Jan. 27, 1993. The serine at about position 30 and the cysteine at about position 37 of SEQ ID NO:13 were conserved in all of these cysteine proteases. Note that these homology calculations did not include the amino acids encoded by DNA primers SEQ ID NO:18 and SEQ ID NO:19. As such, the region used in the homology calculations spanned from about amino acid position 6 through 41 of SEQ ID NO:13.

Example 7

This Example discloses the production of a recombinant cell of the present invention and its use to produce a filariid nematode cysteine protease protein of the present invention.

Recombinant molecule ptrcHis-nDiCP$_{142}$, containing nucleotides from about positions 2 through 143 of nDiCP$_{142}$ (as numbered in SEQ ID NO:12) operatively linked to trc transcription control sequences and to a fusion sequence encoding a poly-histidine segment comprising 6 histidines was produced in the following manner. An about 142-nucleotide DNA fragment containing nucleotides spanning from about 2 through about 143 of nDiCP$_{143}$ (as numbered in SEQ ID NO:12), denoted nDiCP$_{142}$, was sequentially digested from nDiCP$_{143}$ with BamHI restriction endonuclease followed by digestion with EcoRI. Nucleic acid molecule nDiCP$_{142}$ was gel purified and directionally subcloned into expression vector pTrcHisA (available from Invitrogen) that had been cleaved with BamHI and EcoRI and subsequently been gel purified. The resulting recombinant molecule, namely ptrcHis-nDiCP$_{142}$, was transformed into *E. coli* to form recombinant cell *E. coli*:ptrcHis-nDiCP$_{142}$.

Recombinant cell *E. coli*:ptrcHis-nDiCP$_{142}$ is cultured in shake flasks containing an enriched bacterial growth medium containing about 0.1 mg/ml ampicillin at about 37° C. When the cells reach an OD$_{600}$ of about 0.3, expression of *E. coli*:ptrcHis-nDiCP$_{42}$ is induced by addition of about 1 mM isopropyl-β-D-thiogalactoside (IPTG), and the cells cultured for about 3 hours at about 37° C. Protein production is monitored by SDS-PAGE of recombinant cell lysates, followed by Coomassie blue staining, using standard techniques. Recombinant cell *E. coli*:ptrcHis-nDiCP$_{142}$ produces a fusion protein, denoted herein as PHIS-PDiCP$_{142}$, that is not produced by cells transformed with the pTrcHisA plasmid lacking a filariid nucleic acid molecule insert.

Example 8

This Example demonstrates that the protease inhibitors bestatin and phosphoramidon are able to inhibit *D. immitis* larval development, particularly molting. Bestatin (available from Enzyme Systems Products, Livermore, Calif.) primarily, if not exclusively, inhibits amino peptidases and other exopeptidases. Phosphoramidon (also available from Enzyme Systems Products) specifically inhibits thermolysin and collagenase as well as metalloendoproteases from *Bacillus subtilis*, *Streptomyces griseus* and *Pseudomonas aeruginosa* microorganisms.

*D. immitis* larvae were cultured in NI media as described, for example, in U.S. patent application Ser. No. 08/153,554, ibid. NI medium contains a 1:1 mixture of NCTC-135 and Iscove's modified Dulbecco medium (available from Sigma Chemical Co., St. Louis, Mo.), 20% SeruMax, 2.5 micrograms (μg) of amphotericin B per ml, 0.1 nanograms (ng) of gentamicin per ml, 50 μg of sulfadiazine per ml and 10 μg of trimethoprim per ml. Larvae, at a concentration of about 200 L3 per milliliter (ml) of NI medium, were distributed in 0.5-ml aliquots into the wells of a 24-well plate. The volume in each well was adjusted to 1 ml using NI medium and 10-millimolar (mM) stocks of bestatin or phosphoramidon, each of which was dissolved in NI media. The final concentration of inhibitor in the culture wells was either 0, 1, 2.5 or 5 mM. Larvae were incubated at about 37° C., 5% CO2 and 95% relative humidity. Larvae were observed daily and the percent molt (% molt) was evaluated at 72 hours. The percent molt was calculated for each well by dividing the number of cuticles by the number of larvae per well and multiplying by 100. There were three wells for each inhibitor concentration and six wells for the untreated control. The results of this study appear in Table 1.

TABLE 1

Effect of Protease Inhibitors on Larval Molting

| Group | Concentration | % molt | s.d. | % reduction | Fi | Sc |
|---|---|---|---|---|---|---|
| Control | NA | 82.6 | 15.8 | NA | NA | NA |
| Bestatin | 1.0 mM | 60.0 | 9.0 | 27.3 | * | |
| | 2.5 mM | 34.8 | 4.3 | 57.9 | * | * |
| | 5.0 mM | 4.9 | 0.9 | 94.1 | * | * |
| Phosphoramidon | 1.0 mM | 42.6 | 2.1 | 48.4 | * | * |
| | 2.5 mM | 12.3 | 1.2 | 85.1 | * | * |
| | 5.0 mM | 0.0 | 0.0 | 100.0 | * | * |

The results indicate that treatment of L3 by bestatin and phosphoramidon significantly reduces the ability of the larvae to molt. An analysis of variance was performed using % molt. The difference overall was significant (P=0.0001). Fisher PLSD (Fi) and Scheffe F-test (Sc) multiple comparisons comparing each group to the control were done after the ANOVA (* represent significant differences of p<0.05, NA=not applicable).

It was also observed that, in general, bestatin-treated larvae moved much more slowly throughout the study compared to controls whereas phosphoramidon-treated larvae were very active compared to controls. Cuticle separation appeared to be occurring in the phosphoramidon-treated larvae, but the larvae could not open up the old cuticle and escape. The phosphoramidon-treated larvae were in poor shape by the end of the study. While not being bound by theory, it is believed that these phenomena suggest two distinct effects and that the inhibitors may be targeting different enzymes.

Example 9

Example 9 describes the isolation and characterization of protein-containing fractions from excretory/secretory (ES) products of *D. immitis* larvae.

ES products from about 11,600 *D. immitis* L3/L4 were collected and concentrated as described, for example, in U.S. patent application Ser. No. 08/153,554, ibid. The buffer was exchanged to 20 mM piperazine-HCl, pH 6.0, 0.005% Brij 35 using a Centriprep 10 (available from Amicon Inc., Beverly, Mass.). The resulting mixture was separated on a Mono-Q column (anion exchange) (available from Pharmacia Biotech Inc., Piscataway, N.J.) equilibrated in 20 μM piperazine-HCl, pH 6.0 using an increasing gradient of sodium chloride. Each fraction was then brought to 0.005% Brij 35. Buffer A was 20 mM piperazine-HCl, pH 6.0. Buffer B was 1 M sodium chloride in 20 mM piperazine-HCl, pH 6.0. The chromatography program was: (a) 0% B for 5 minutes; (b) 0% to about 50% B over 25 minutes; (c) hold 3 minutes; (d) about 50% to 100% B over 5 minutes. The flow rate was 0.5 ml per minute. Fractions were collected every minute.

The collected fractions were assayed for metalloprotease activity using the fluorogenic compound H-phenylalanine-7-amido-4-methylcoumarin (H-Phe-AMC). The assay was conducted as follows. A stock solution of 10 mM H-Phe-AMC in dimethyl sulfoxide (DMSO) was diluted 1:200 with 100 mM Tris-HCl, pH 7.0. About 100 microliters (μl) of the diluted stock solution was placed in each of a desired number of wells in a 96-well microtiter plate. To each well was added 25 μl of the fractions, or control samples, to be tested. The resulting mixture was incubated at about 37° C. for at least 2 hours. The microtiter plate was then placed on a UV light box and photographed to identify fractions in which AMC was cleaved (released AMC glows under such conditions).

Fractions 20 and 21 collected from the anion exchange both exhibited metalloproteolytic activity. An aliquot of fraction 21 was concentrated and evaluated by SDS-PAGE (14% Tris-glycine). One major band was detected that migrated with an apparently molecule weight of about 60 kD.

Anion exchange fraction 21 was then applied to size exclusion chromatography as described in U.S. patent application Ser. No. 08/153,554, ibid. Specifically, Fraction 21 from the anion exchange column was applied to a TSK 3000 SW column (available from Beckman Instruments Inc., Fullerton, Calif.) in 50 mM Tris-HCl, pH 7.5, 150 mM sodium chloride, at a flow rate of 0.5 ml per minute. Fractions were collected every 0.5 minutes. When assayed using the microtiter plate fluorescent assay, fractions 21 and 22 were positive. The relative time of elution of these fractions was very close to the elution time of bovine serum albumin, which has a molecular weight of about 62 to 66 kD.

Anion exchange fraction 21 was also submitted to isoelectric focussing under "native" conditions. The resultant gel was sliced into 1 mm fractions and the strips assayed by the microtiter plate fluorescent assay. The active fraction was in a region having a pI of about 6.8.

In a separate study, ES from about 2500 larvae was submitted to electrophoresis through each of two lanes of Novex Zymogel (available from Novex, San Diego, Calif.). Zymogel contains about 0.1 percent gelatin. The two lanes were soaked in 2.5% Triton X-100 for about 30 minutes and subsequently washed in reaction buffer (50 mM Tris-HCl, pH 7.0, 5 mM calcium chloride, 0.02% Brij 35 and 200 mM sodium chloride) for about 30 minutes. One lane was then incubated in reaction buffer at about 37° C. for 66 hours. The other lane was incubated in reaction buffer containing 2 mM EDTA for the same amount of time. Both lanes were then stained in 0.5% CBB-R250, 40% methanol, 10% acetic acid and destained in 40% methanol, 10% acetic acid in order to detect collagenase activity. Activity was identified by a clear zone in a blue background. ES proteins displaying metalloprotease activity that was completely inhibited by EDTA migrated with apparent molecular weights of about 60 kD, about 95 kD and at least about 200 kD.

SEQUENCE LISTING

The following Sequence Listing is submitted pursuant to 37 CFR §1.821. A copy in computer readable form is also submitted herewith.

The content of the paper and computer readable copies of this Sequence Listing are the same.

SEQUENCE LISTING ( 1 ) GENERAL INFORMATION:

( i i i ) NUMBER OF SEQUENCES: 19

( 2 ) INFORMATION FOR SEQ ID NO:1:

( i ) SEQUENCE CHARACTERISTICS:
        ( A ) LENGTH: 1299 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:1:

```
TTTTTTTTT  TTTTTTTGT   TTCATTGTTC  AGTCAGTGGA  AAATTATCGA  ACGCAGAAAG    60
CATCACGAAA  TACGTTAGAT  CACATCAAAC  AACTTATCAC  CTTGAACGTA  CAAAGAGAGA   120
TTGGAAACAT  AGATGATAAG  ACATTAGCTG  ATGAAATAGT  ATTACAACGA  CGGGATCCTG   180
AGGCAAAATG  GCATCATAAT  GAACTATTCA  TTAATGATCC  AGATGCATAC  TATCAAGGCG   240
ATGTCGATTT  GTCGGAAAAA  CAAGCCGAAA  TTCTAAGCGA  ACATTTTAAA  AATGAAATTG   300
CTTTAACAGA  GAAAGACGAC  ACAATAATAC  GGCGAAAAAA  GAGCATTGGT  CGTGAACCAT   360
TTTACGTAAG  ATGGAATCAT  AAACGTCCCA  TTAGCTATGA  ATTTGCGGAA  AGTATTCCAT   420
TAGAAACACG  TAGAAAAATT  CGTTCAGCAA  TAGCAATGTG  GGAAGAACGA  ACATGCATAC   480
GATTCCAAGA  AAATGGCCCA  AATGTAGATC  GAATTGAATT  TTACGACGGT  GGCGGTTGTT   540
CAAGTTTTGT  CGGCCGAACA  GGAGGGAATT  TCAATTTCAA  CACCAGGATG  TGATATTATT   600
GGTATTATAT  CACATGAAAT  TGGTCATACT  TTAGGAATAT  TTCATGAGCA  AGCACGTCGT   660
GATCAAAAAA  ATCATATTTT  TATTAATTAC  AACAATATTC  CATCAAGCCG  TTGGAACAAT   720
TTTTTCCAT   TATCAGAATA  TGAAGCTGAT  ATGTTTAATT  TACCTTATGA  TACAGGATCA   780
GTAATGCACT  ATGGTTCATA  CGGATTTGCA  AGAAATCCGT  ATGAACCAAC  TATTACAACA   840
CGTGATAAAT  TTCAACAGTA  CACAATTGGG  CAACGTGAAG  GGCCATCATT  TCTGGATTAT   900
GCATCTGTTA  AGCTTTATCT  ACAAACGCAT  TAATGATATT  GTTATCAAAT  GGATGATAAT   960
TTCAATAAGT  ATAAACAGCG  CTTATCGTTG  TACAGAACAA  TGTGCTGATA  TGCACTGCGA  1020
TCATAATGGT  TATCCGGATC  CTAATAATTG  CGCGAAATGC  TTGTGTCCAG  ATGGTTTTGC  1080
TGGTCGTACC  TGTCAATTTG  TTCAATATAC  ATCTTGCGGA  GCTCTCATTA  AGGTAAGTAT  1140
TGTCTTTTGA  CCTCTTCTCT  GACTAAAATA  TAAGTTAAGC  ATATGTATCT  TCCGTCTAAT  1200
GATTTCTTG   ATTTTGATTT  GTTCAATGCT  CTTCTTGATA  ATAATATAAA  AATTTTTGAA  1260
AATAAAGTTA  ACTTTTGGTC  AAAAAAAAAA  AAAAAAAA                            1299
```

( 2 ) INFORMATION FOR SEQ ID NO:2:

( i ) SEQUENCE CHARACTERISTICS:
    ( A ) LENGTH: 2126 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:2:

```
GAAAGCATCA CGAAATACGT TAGATCACAT CAAACAACTT ATCACCTTGA ACGTACAAAG      60
AGAGATTGGA ACATAGATG  ATAAGACATT AGCTGATGAA ATAGTATTAC AACGACGGGA     120
TCCTGAGGCA AAATGGCATC ATAATGAACT ATTCATTAAT GATCCAGATG CATACTATCA     180
AGGCGATGTC GATTTGTCGG AAAAACAAGC CGAAATTCTA AGCGAACATT TTAAAAATGA     240
AATTGCTTTA ACAGAGAAAG ACGACACAAT AATACGGCGA AAAAGAGCA  TTGGTCGTGA     300
ACCATTTTAC GTAAGATGGA ATCATAAACG TCCCATTAGC TATGAATTTG CGGAAAGTAT     360
TCCATTAGAA ACACGTAGAA AAATTCGTTC AGCAATAGCA ATGTGGGAAG AACGAACATG     420
CATACGATTC CAAGAAAATG GCCCAAATGT AGATCGAATT GAATTTTACG ACGGTGGCGG     480
TTGTTCAAGT TTTGTCGGCC GAACAGGAGG GAATTTCAAT TCAACACCA  GGATGTGATA     540
TTATTGGTAT TATATCACAT GAAATTGGTC ATACTTTAGG AATATTTCAT GAGCAAGCAC     600
GTCGTGATCA AAAAAATCAT ATTTTTATTA ATTACAACAA TATTCCATCA AGCCGTTGGA     660
ACAATTTTTT TCCATTATCA GAATATGAAG CTGATATGTT TAATTTACCT TATGATACAG     720
GATCAGTAAT GCACTATGGT TCATACGGAT TTGCAAGAAA TCCGTATGAA CCAACTATTA     780
CAACACGTGA TAAATTTCAA CAGTACACAA TTGGGCAACG TGAAGGGCCA TCATTTCTGG     840
ATTATGCATC TGATAAACAG CGCTTATCGT TGTACAGAAC AATGTGCTGA TATGCACTGC     900
GATCATAATG GTTATCCGGA TCCTAATAAT TGCGCGAAAT GCTTGTGTCC AGATGGTTTT     960
GCTGGTCGTA CCTGTCAATT TGTTCAATAT ACATCTTGCG GAGCTCTCAT TAAGGCGAGG    1020
AAAATGCCTG TTACGATTTC GAGCCCAAAT TATCCAAACT TCTTCAATGT TGGTGATCAA    1080
TGTATTTGGT TGCTTACAGC TCCACGCGTG ATTCGTAAAT TTGCAGTTTG TTGAACAATT    1140
TCAATTACAA TGTGAAGATA CGTGTGATAA ATCCTATGTA GAAGTGAAAG CTGACGCTGA    1200
TTTTCGACCT ACTGGATATC GATTTGTTG  TTCGCGAGTG CCACGTCATA TTTTTCAATC    1260
TGCGACAAAC GAGATGGTAG TAATATTTCG CGGTTTTGGT GATGCGGGAA ATGGCTTTAA    1320
AGCTAAAATT TGGTCAAACG TAGATGATGA TATAGCTAAT ACAATTGTAA CAACTGAAAT    1380
GGCAAAAATT TCGGAAAAAA TACCGAAGCT AACAGTTCCA ATAGTTAAAA CTATTACCAC    1440
TCCTACAATA ACAACTACTA CTGCTTTCAT GATATCACCC AAGAAAGGCA ATGTCACCGC    1500
CACGAGAGTT GCTATCACTA CTACGCCGAC TACTACAATT ACTACGACTA TTGCCGGTAC    1560
GTACCAATCA CCGTAACTAA TAATACTACA CCTGTAGTAA GTGAAACTTT ACCATCATTG    1620
CCAGTCAAGA TTCGAAACAA AATAGGTGCA TGCGAATGTG GTGAATGGAC AGAATGGACA    1680
GGTCCATGCT CTCAAGAATG TGGCGGTTGC GGAAAACGTC TTCGAACACG TCAGTGTTCA    1740
TCAGATACGG AATGTAGAAC AGAAGAAAAA CGTGCGTGTG CTTTTAAGTT TGCCCATACG    1800
GGACTAATTT CCTTATCAAT AATGGAGAGT TTCATATACT TTGGAAGGGC TGCTGTGTTG    1860
GTCTATTCCG ATCGGGAGAT ATGTGTTCAG CACTTGATGA TAACGAGAAT CCATTTCTGA    1920
AATTTCTAGA ATCACTGTTG AACATGCAAG ATTCTCGAAA AACGATAAT  TTGCCTGACT    1980
CGAAAAAGAA GTGATTGAAT GATTCGATAA TATTGATTAA TAAACGGGT  TGTATTCTCG    2040
```

```
TCATAGAGTA TCCGTTGATG TTTTTATCCA AAAAATTCTC TTGCTTTTAA TTATTGTGAA        2100

TAAAACTTTT GTTTACCCAA AAAAAA                                             2126
```

( 2 ) INFORMATION FOR SEQ ID NO:3:

( i ) SEQUENCE CHARACTERISTICS:
        ( A ) LENGTH: 191 amino acids
        ( B ) TYPE: amino acid
        ( D ) TOPOLOGY: linear ( i i ) MOLECULE TYPE: protein ( x i ) SEQUENCE DESCRIPTION: SEQ ID NO:3:

```
Cys Phe Ile Val Gln Ser Val Glu Asn Tyr Arg Thr Gln Lys Ala Ser
 1           5                  10                  15

Arg Asn Thr Leu Asp His Ile Lys Gln Leu Ile Thr Leu Asn Val Gln
            20                  25                  30

Arg Glu Ile Gly Asn Ile Asp Asp Lys Thr Leu Ala Asp Glu Ile Val
        35                  40                  45

Leu Gln Arg Arg Asp Pro Glu Ala Lys Trp His His Asn Glu Leu Phe
    50                  55                  60

Ile Asn Asp Pro Asp Ala Tyr Tyr Gln Gly Asp Val Asp Leu Ser Glu
65                  70                  75                  80

Lys Gln Ala Glu Ile Leu Ser Glu His Phe Lys Asn Glu Ile Ala Leu
                85                  90                  95

Thr Glu Lys Asp Asp Thr Ile Ile Arg Arg Lys Lys Ser Ile Gly Arg
            100                 105                 110

Glu Pro Phe Tyr Val Arg Trp Asn His Lys Arg Pro Ile Ser Tyr Glu
        115                 120                 125

Phe Ala Glu Ser Ile Pro Leu Glu Thr Arg Arg Lys Ile Arg Ser Ala
    130                 135                 140

Ile Ala Met Trp Glu Glu Arg Thr Cys Ile Arg Phe Gln Glu Asn Gly
145                 150                 155                 160

Pro Asn Val Asp Arg Ile Glu Phe Tyr Asp Gly Gly Gly Cys Ser Ser
                165                 170                 175

Phe Val Gly Arg Thr Gly Gly Asn Phe Asn Phe Asn Thr Arg Met
            180                 185                 190
```

( 2 ) INFORMATION FOR SEQ ID NO:4:

( i ) SEQUENCE CHARACTERISTICS:
        ( A ) LENGTH: 141 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Ile Glu Leu Asn Phe Thr Thr Val Ala Val Val Gln Val Leu Ser Ala
 1           5                  10                  15

Glu Gln Glu Gly Ile Ser Ile Ser Thr Pro Gly Cys Asp Ile Ile Gly
            20                  25                  30

Ile Ile Ser His Glu Ile Gly His Thr Leu Gly Ile Phe His Glu Gln
        35                  40                  45

Ala Arg Arg Asp Gln Lys Asn His Ile Phe Ile Asn Tyr Asn Asn Ile
    50                  55                  60

Pro Ser Ser Arg Trp Asn Asn Phe Phe Pro Leu Ser Glu Tyr Glu Ala
65                  70                  75                  80
```

```
Asp  Met  Phe  Asn  Leu  Pro  Tyr  Asp  Thr  Gly  Ser  Val  Met  His  Tyr  Gly
               85                  90                       95

Ser  Tyr  Gly  Phe  Ala  Arg  Asn  Pro  Tyr  Glu  Pro  Thr  Ile  Thr  Thr  Arg
               100                 105                      110

Asp  Lys  Phe  Gln  Gln  Tyr  Thr  Ile  Gly  Gln  Arg  Glu  Gly  Pro  Ser  Phe
               115                 120                      125

Leu  Asp  Tyr  Ala  Ser  Val  Lys  Leu  Tyr  Leu  Gln  Thr  His
               130                 135                 140
```

(2) INFORMATION FOR SEQ ID NO:5:

(i) SEQUENCE CHARACTERISTICS:
        (A) LENGTH: 121 amino acids
        (B) TYPE: amino acid
        (D) TOPOLOGY: linear (ii) MOLECULE TYPE: protein (xi) SEQUENCE DESCRIPTION: SEQ ID NO:5:

```
Cys  Thr  Met  Val  His  Thr  Asp  Leu  Gln  Glu  Ile  Arg  Met  Asn  Gln  Leu
1                   5                   10                      15

Leu  Gln  His  Val  Ile  Asn  Phe  Asn  Ser  Thr  Gln  Leu  Gly  Asn  Val  Lys
               20                  25                       30

Gly  His  His  Phe  Trp  Ile  Met  His  Leu  Leu  Ser  Phe  Ile  Tyr  Lys  Arg
               35                  40                       45

Ile  Asn  Asp  Ile  Val  Ile  Lys  Trp  Met  Ile  Ile  Ser  Ile  Ser  Ile  Asn
     50                  55                       60

Ser  Ala  Tyr  Arg  Cys  Thr  Glu  Gln  Cys  Ala  Asp  Met  His  Cys  Asp  His
65                       70                  75                      80

Asn  Gly  Tyr  Pro  Asp  Pro  Asn  Asn  Cys  Ala  Lys  Cys  Leu  Cys  Pro  Asp
               85                  90                       95

Gly  Phe  Ala  Gly  Arg  Thr  Cys  Gln  Phe  Val  Gln  Tyr  Thr  Ser  Cys  Gly
               100                 105                      110

Ala  Leu  Ile  Lys  Val  Ser  Ile  Val  Phe
               115                 120
```

(2) INFORMATION FOR SEQ ID NO:6:

(i) SEQUENCE CHARACTERISTICS:
        (A) LENGTH: 178 amino acids
        (B) TYPE: amino acid
        (D) TOPOLOGY: linear (ii) MOLECULE TYPE: protein (xi) SEQUENCE DESCRIPTION: SEQ ID NO:6:

```
Lys  Ala  Ser  Arg  Asn  Thr  Leu  Asp  His  Ile  Lys  Gln  Leu  Ile  Thr  Leu
1                   5                   10                      15

Asn  Val  Gln  Arg  Glu  Ile  Gly  Asn  Ile  Asp  Asp  Lys  Thr  Leu  Ala  Asp
               20                  25                       30

Glu  Ile  Val  Leu  Gln  Arg  Arg  Asp  Pro  Glu  Ala  Lys  Trp  His  His  Asn
               35                  40                       45

Glu  Leu  Phe  Ile  Asn  Asp  Pro  Asp  Ala  Tyr  Tyr  Gln  Gly  Asp  Val  Asp
     50                  55                       60

Leu  Ser  Glu  Lys  Gln  Ala  Glu  Ile  Leu  Ser  Glu  His  Phe  Lys  Asn  Glu
65                       70                  75                      80

Ile  Ala  Leu  Thr  Glu  Lys  Asp  Asp  Thr  Ile  Ile  Arg  Arg  Lys  Lys  Ser
               85                  90                       95

Ile  Gly  Arg  Glu  Pro  Phe  Tyr  Val  Arg  Trp  Asn  His  Lys  Arg  Pro  Ile
               100                 105                      110
```

Ser Tyr Glu Phe Ala Glu Ser Ile Pro Leu Glu Thr Arg Arg Lys Ile
115                     120                 125

Arg Ser Ala Ile Ala Met Trp Glu Glu Arg Thr Cys Ile Arg Phe Gln
130                 135                 140

Glu Asn Gly Pro Asn Val Asp Arg Ile Glu Phe Tyr Asp Gly Gly Gly
145             150                 155                 160

Cys Ser Ser Phe Val Gly Arg Thr Gly Gly Asn Phe Asn Phe Asn Thr
                165             170                 175

Arg Met ( 2 ) INFORMATION FOR SEQ ID NO:7:

( i ) SEQUENCE CHARACTERISTICS:
       ( A ) LENGTH: 145 amino acids
       ( B ) TYPE: amino acid
       ( D ) TOPOLOGY: linear ( i i ) MOLECULE TYPE: protein ( x i ) SEQUENCE DESCRIPTION: SEQ ID NO:7:

Ile Glu Leu Asn Phe Thr Thr Val Ala Val Val Gln Val Leu Ser Ala
1               5                   10                  15

Glu Gln Glu Gly Ile Ser Ile Ser Thr Pro Gly Cys Asp Ile Ile Gly
                20                  25                  30

Ile Ile Ser His Glu Ile Gly His Thr Leu Gly Ile Phe His Glu Gln
            35                  40                  45

Ala Arg Arg Asp Gln Lys Asn His Ile Phe Ile Asn Tyr Asn Asn Ile
        50                  55                  60

Pro Ser Ser Arg Trp Asn Asn Phe Phe Pro Leu Ser Glu Tyr Glu Ala
65                  70                  75                  80

Asp Met Phe Asn Leu Pro Tyr Asp Thr Gly Ser Val Met His Tyr Gly
                85                  90                  95

Ser Tyr Gly Phe Ala Arg Asn Pro Tyr Glu Pro Thr Ile Thr Thr Arg
                100                 105                 110

Asp Lys Phe Gln Gln Tyr Thr Ile Gly Gln Arg Glu Gly Pro Ser Phe
            115                 120                 125

Leu Asp Tyr Ala Ser Asp Lys Gln Arg Leu Ser Leu Tyr Arg Thr Met
        130                 135                 140

Cys

145

( 2 ) INFORMATION FOR SEQ ID NO:8:

( i ) SEQUENCE CHARACTERISTICS:
       ( A ) LENGTH: 134 amino acids
       ( B ) TYPE: amino acid
       ( D ) TOPOLOGY: linear ( i i ) MOLECULE TYPE: protein ( x i ) SEQUENCE DESCRIPTION: SEQ ID NO:8:

Cys Thr Met Val His Thr Asp Leu Gln Glu Ile Arg Met Asn Gln Leu
1               5                   10                  15

Leu Gln His Val Ile Asn Phe Asn Ser Thr Gln Leu Gly Asn Val Lys
                20                  25                  30

Gly His His Phe Trp Ile Met His Leu Ile Asn Ser Ala Tyr Arg Cys
            35                  40                  45

Thr Glu Gln Cys Ala Asp Met His Cys Asp His Asn Gly Tyr Pro Asp

|   |   |   | 50 |   |   |   | 55 |   |   |   | 60 |   |   |
|---|---|---|---|---|---|---|---|---|---|---|---|---|---|

Pro  Asn  Asn  Cys  Ala  Lys  Cys  Leu  Cys  Pro  Asp  Gly  Phe  Ala  Gly  Arg
65                   70                  75                       80

Thr  Cys  Gln  Phe  Val  Gln  Tyr  Thr  Ser  Cys  Gly  Ala  Leu  Ile  Lys  Ala
              85                       90                       95

Arg  Lys  Met  Pro  Val  Thr  Ile  Ser  Ser  Pro  Asn  Tyr  Pro  Asn  Phe  Phe
              100                      105                      110

Asn  Val  Gly  Asp  Gln  Cys  Ile  Trp  Leu  Leu  Thr  Ala  Pro  Arg  Val  Ile
              115                      120                      125

Arg  Lys  Phe  Ala  Val  Cys
              130

( 2 ) INFORMATION FOR SEQ ID NO:9:

( i ) SEQUENCE CHARACTERISTICS:
      ( A ) LENGTH: 154 amino acids
      ( B ) TYPE: amino acid
      ( D ) TOPOLOGY: linear ( i i ) MOLECULE TYPE: protein ( x i ) SEQUENCE DESCRIPTION: SEQ ID NO:9:

Phe  Val  Asn  Leu  Gln  Phe  Val  Glu  Gln  Phe  Gln  Leu  Gln  Cys  Glu  Asp
1                   5                   10                      15

Thr  Cys  Asp  Lys  Ser  Tyr  Val  Glu  Val  Lys  Ala  Asp  Ala  Asp  Phe  Arg
              20                       25                      30

Pro  Thr  Gly  Tyr  Arg  Phe  Cys  Cys  Ser  Arg  Val  Pro  Arg  His  Ile  Phe
              35                       40                      45

Gln  Ser  Ala  Thr  Asn  Glu  Met  Val  Val  Ile  Phe  Arg  Gly  Phe  Gly  Asp
50                                   55                       60

Ala  Gly  Asn  Gly  Phe  Lys  Ala  Lys  Ile  Trp  Ser  Asn  Val  Asp  Asp  Asp
65                   70                  75                       80

Ile  Ala  Asn  Thr  Ile  Val  Thr  Thr  Glu  Met  Ala  Lys  Ile  Ser  Glu  Lys
              85                       90                      95

Ile  Pro  Lys  Leu  Thr  Val  Pro  Ile  Val  Lys  Thr  Ile  Thr  Thr  Pro  Thr
              100                      105                      110

Ile  Thr  Thr  Thr  Thr  Ala  Phe  Met  Ile  Ser  Pro  Lys  Lys  Gly  Asn  Val
              115                      120                      125

Thr  Ala  Thr  Arg  Asx  Ala  Ile  Thr  Thr  Thr  Pro  Thr  Thr  Thr  Ile  Thr
              130                      135                      140

Thr  Thr  Ile  Ala  Gly  Thr  Tyr  Gln  Ser  Pro
145                      150

( 2 ) INFORMATION FOR SEQ ID NO:10:

( i ) SEQUENCE CHARACTERISTICS:
      ( A ) LENGTH: 163 amino acids
      ( B ) TYPE: amino acid
      ( D ) TOPOLOGY: linear ( i i ) MOLECULE TYPE: protein ( x i ) SEQUENCE DESCRIPTION: SEQ ID NO:10:

Asn  Tyr  Tyr  His  Ser  Tyr  Asn  Asn  Tyr  Tyr  Cys  Phe  His  Asp  Ile
1                   5                   10                      15

Thr  Gln  Glu  Arg  Gln  Cys  His  Arg  His  Glu  Ser  Cys  Tyr  His  Tyr  Tyr
              20                       25                      30

Ala  Asp  Tyr  Tyr  Asn  Tyr  Tyr  Asp  Tyr  Cys  Arg  Tyr  Val  Pro  Ile  Thr
              35                       40                      45

```
Val  Thr  Asn  Asn  Thr  Thr  Pro  Val  Val  Ser  Glu  Thr  Leu  Pro  Ser  Leu
     50                       55                      60

Pro  Val  Lys  Ile  Arg  Asn  Lys  Ile  Gly  Ala  Cys  Glu  Cys  Gly  Glu  Trp
65                       70                  75                           80

Thr  Glu  Trp  Thr  Gly  Pro  Cys  Ser  Gln  Glu  Cys  Gly  Gly  Cys  Gly  Lys
               85                       90                           95

Arg  Leu  Arg  Thr  Arg  Gln  Cys  Ser  Ser  Asp  Thr  Glu  Cys  Arg  Thr  Glu
               100                      105                 110

Glu  Lys  Arg  Ala  Cys  Ala  Phe  Lys  Phe  Ala  His  Thr  Gly  Leu  Ile  Ser
          115                      120                      125

Leu  Ser  Ile  Met  Glu  Ser  Phe  Ile  Tyr  Phe  Gly  Arg  Ala  Ala  Val  Leu
     130                      135                      140

Val  Tyr  Ser  Asp  Arg  Glu  Ile  Cys  Val  Gln  His  Leu  Met  Ile  Thr  Arg
145                      150                      155                      160

Ile  His  Phe
```

( 2 ) INFORMATION FOR SEQ ID NO:11:

( i ) SEQUENCE CHARACTERISTICS:
( A ) LENGTH: 638 amino acids
( B ) TYPE: amino acid
( D ) TOPOLOGY: linear ( i i ) MOLECULE TYPE: protein ( x i ) SEQUENCE DESCRIPTION: SEQ ID NO:11:

```
Lys  Ala  Ser  Arg  Asn  Thr  Leu  Asp  His  Ile  Lys  Gln  Leu  Ile  Thr  Leu
1                    5                        10                      15

Asn  Val  Gln  Arg  Glu  Ile  Gly  Asn  Ile  Asp  Asp  Lys  Thr  Leu  Ala  Asp
               20                      25                      30

Glu  Ile  Val  Leu  Gln  Arg  Arg  Asp  Pro  Glu  Ala  Lys  Trp  His  His  Asn
               35                      40                      45

Glu  Leu  Phe  Ile  Asn  Asp  Pro  Asp  Ala  Tyr  Tyr  Gln  Gly  Asp  Val  Asp
     50                       55                      60

Leu  Ser  Glu  Lys  Gln  Ala  Glu  Ile  Leu  Ser  Glu  His  Phe  Lys  Leu  Asn
65                       70                      75                       80

Glu  Ile  Ala  Leu  Thr  Glu  Lys  Asp  Asp  Thr  Ile  Ile  Arg  Arg  Lys  Lys
               85                      90                      95

Ser  Ile  Gly  Arg  Glu  Pro  Phe  Tyr  Val  Arg  Trp  Asn  His  Lys  Arg  Pro
               100                     105                     110

Ile  Ser  Tyr  Glu  Phe  Ala  Glu  Ser  Ile  Pro  Leu  Glu  Thr  Arg  Arg  Lys
          115                      120                     125

Ile  Arg  Ser  Ala  Ile  Ala  Met  Trp  Glu  Glu  Arg  Thr  Cys  Ile  Arg  Phe
     130                      135                      140

Gln  Glu  Asn  Gly  Pro  Asn  Val  Asp  Arg  Ile  Glu  Phe  Tyr  Asp  Gly  Gly
145                      150                      155                      160

Gly  Cys  Ser  Ser  Phe  Val  Gly  Arg  Gln  Glu  Gly  Ile  Ser  Ile  Ser  Thr
                    165                      170                     175

Pro  Gly  Cys  Asp  Ile  Ile  Gly  Ile  Ile  Ser  His  Glu  Ile  Gly  His  Thr
               180                      185                      190

Leu  Gly  Ile  Phe  His  Glu  Gln  Ala  Arg  Arg  Asp  Gln  Lys  Asn  His  Ile
          195                      200                      205

Phe  Ile  Asn  Tyr  Asn  Asn  Ile  Pro  Ser  Ser  Arg  Trp  Asn  Asn  Phe  Phe
     210                      215                      220

Pro  Leu  Ser  Glu  Tyr  Glu  Ala  Asp  Met  Phe  Asn  Leu  Pro  Tyr  Asp  Thr
225                      230                      235                      240
```

| | | | | | | | | | | | | | | |
|---|---|---|---|---|---|---|---|---|---|---|---|---|---|---|
| Gly | Ser | Val | Met | His 245 | Tyr | Gly | Ser | Tyr 250 | Gly | Phe | Ala | Arg | Asn | Pro 255 | Tyr |
| Glu | Pro | Thr | Ile 260 | Thr | Thr | Arg | Asp | Lys 265 | Phe | Gln | Gln | Tyr 270 | Thr | Ile | Gly |
| Gln | Arg | Glu 275 | Gly | Pro | Ser | Phe | Leu 280 | Asp | Met | His | Leu | Ile 285 | Asn | Ser | Ala |
| Tyr | Arg 290 | Cys | Thr | Glu | Gln | Cys 295 | Ala | Asp | Met | His | Cys 300 | Asp | His | Asn | Gly |
| Tyr 305 | Pro | Asp | Pro | Asn | Asn 310 | Cys | Ala | Lys | Cys | Leu 315 | Cys | Pro | Asp | Gly | Phe 320 |
| Ala | Gly | Arg | Thr | Cys 325 | Gln | Phe | Val | Gln | Tyr 330 | Thr | Ser | Cys | Gly | Ala 335 | Leu |
| Ile | Lys | Ala | Arg 340 | Lys | Met | Pro | Val | Thr 345 | Ile | Ser | Ser | Pro | Asn 350 | Tyr | Pro |
| Asn | Phe | Phe 355 | Asn | Tyr | Gly | Asp | Gln 360 | Cys | Ile | Trp | Leu | Leu 365 | Thr | Ala | Pro |
| Arg | Val 370 | Phe | Val | Asn | Leu | Gln 375 | Phe | Val | Glu | Gln | Phe 380 | Gln | Leu | Gln | Cys |
| Glu 385 | Asp | Thr | Cys | Asp | Lys 390 | Ser | Tyr | Val | Glu | Val 395 | Lys | Ala | Asp | Ala | Asp 400 |
| Phe | Arg | Pro | Thr | Gly 405 | Tyr | Arg | Phe | Cys | Cys 410 | Ser | Arg | Val | Pro | Arg 415 | His |
| Ile | Phe | Gln | Ser 420 | Ala | Thr | Asn | Glu | Met 425 | Val | Val | Ile | Phe | Arg 430 | Gly | Phe |
| Gly | Asp | Ala 435 | Gly | Asn | Gly | Phe | Lys 440 | Ala | Lys | Ile | Trp | Ser 445 | Asn | Val | Asp |
| Asp | Asp 450 | Ile | Ala | Asn | Thr | Ile 455 | Val | Thr | Thr | Glu | Met 460 | Ala | Lys | Ile | Ser |
| Glu 465 | Lys | Ile | Pro | Lys | Leu 470 | Thr | Val | Pro | Ile | Val 475 | Lys | Thr | Ile | Thr | Thr 480 |
| Pro | Thr | Ile | Thr | Thr 485 | Thr | Thr | Ala | Phe | Met 490 | Ile | Ser | Pro | Lys | Lys 495 | Gly |
| Asn | Val | Thr | Ala 500 | Thr | Arg | Val | Ala | Ile 505 | Thr | Thr | Thr | Pro | Thr 510 | Thr | Thr |
| Ile | Thr | Thr 515 | Thr | Ile | Ala | Gly | Thr 520 | Tyr | Gln | Ser | Val | Thr 525 | Asn | Asn | Thr |
| Thr | Pro 530 | Val | Val | Ser | Glu | Thr 535 | Leu | Pro | Ser | Leu | Pro 540 | Val | Lys | Ile | Arg |
| Asn 545 | Lys | Ile | Gly | Ala | Cys 550 | Glu | Cys | Gly | Glu | Trp 555 | Thr | Glu | Trp | Thr | Gly 560 |
| Pro | Cys | Ser | Gln | Glu 565 | Cys | Gly | Gly | Cys | Gly 570 | Lys | Arg | Leu | Arg | Thr 575 | Arg |
| Gln | Cys | Ser | Ser 580 | Asp | Thr | Glu | Cys | Arg 585 | Thr | Glu | Glu | Lys | Arg 590 | Ala | Cys |
| Ala | Phe | Lys 595 | Phe | Ala | His | Thr | Gly 600 | Leu | Ile | Ser | Leu | Ser 605 | Ile | Met | Glu |
| Ser | Phe 610 | Ile | Tyr | Phe | Gly | Arg 615 | Ala | Ala | Val | Leu | Val 620 | Tyr | Ser | Asp | Arg |
| Glu 625 | Ile | Cys | Val | Gln | His 630 | Leu | Met | Ile | Thr | Arg 635 | Ile | His | Phe | | |

(2) INFORMATION FOR SEQ ID NO:12:

(i) SEQUENCE CHARACTERISTICS:
(A) LENGTH: 143 base pairs ( B ) TYPE: nucleic acid
( C ) STRANDEDNESS: single
( D ) TOPOLOGY: linear ( i i ) MOLECULE TYPE: DNA (genomic)

( i x ) FEATURE:
( A ) NAME/KEY: CDS
( B ) LOCATION: 1..143

( x i ) SEQUENCE DESCRIPTION: SEQ ID NO:12:

| GGA | TCC | TGT | GGT | TCA | TGT | TGG | GCT | TTT | TCT | GTT | ACT | GGC | AAT | ATT | GCA | 48 |
|---|---|---|---|---|---|---|---|---|---|---|---|---|---|---|---|---|
| Gly | Ser | Cys | Gly | Ser | Cys | Trp | Ala | Phe | Ser | Val | Thr | Gly | Asn | Ile | Ala | |
| 1 | | | | 5 | | | | | 10 | | | | | 15 | | |

| AGT | CTC | TGG | GCT | ATT | AAA | ACA | GGT | GAT | TTG | ATA | TCG | CTT | TCC | GAG | CAA | 96 |
|---|---|---|---|---|---|---|---|---|---|---|---|---|---|---|---|---|
| Ser | Leu | Trp | Ala | Ile | Lys | Thr | Gly | Asp | Leu | Ile | Ser | Leu | Ser | Glu | Gln | |
| | | | 20 | | | | | 25 | | | | | 30 | | | |

| GAA | TTG | ATT | GAT | TGT | GAT | GTG | GTT | GAT | GAG | GGC | TGC | AAC | GGC | GGC | TA | 143 |
|---|---|---|---|---|---|---|---|---|---|---|---|---|---|---|---|---|
| Glu | Leu | Ile | Asp | Cys | Asp | Val | Val | Asp | Glu | Gly | Cys | Asn | Gly | Gly | | |
| | | | 35 | | | | 40 | | | | | 45 | | | | |

( 2 ) INFORMATION FOR SEQ ID NO:13:

( i ) SEQUENCE CHARACTERISTICS:
( A ) LENGTH: 47 amino acids
( B ) TYPE: amino acid
( D ) TOPOLOGY: linear ( i i ) MOLECULE TYPE: protein ( x i ) SEQUENCE DESCRIPTION: SEQ ID NO:13:

| Gly | Ser | Cys | Gly | Ser | Cys | Trp | Ala | Phe | Ser | Val | Thr | Gly | Asn | Ile | Ala |
|---|---|---|---|---|---|---|---|---|---|---|---|---|---|---|---|
| 1 | | | | 5 | | | | | 10 | | | | | 15 | |

| Ser | Leu | Trp | Ala | Ile | Lys | Thr | Gly | Asp | Leu | Ile | Ser | Leu | Ser | Glu | Gln |
|---|---|---|---|---|---|---|---|---|---|---|---|---|---|---|---|
| | | | 20 | | | | | 25 | | | | | 30 | | |

| Glu | Leu | Ile | Asp | Cys | Asp | Val | Val | Asp | Glu | Gly | Cys | Asn | Gly | Gly |
|---|---|---|---|---|---|---|---|---|---|---|---|---|---|---|
| | | | 35 | | | | 40 | | | | | 45 | | |

( 2 ) INFORMATION FOR SEQ ID NO:14:

( i ) SEQUENCE CHARACTERISTICS:
( A ) LENGTH: 18 base pairs
( B ) TYPE: nucleic acid
( C ) STRANDEDNESS: single
( D ) TOPOLOGY: linear ( i i ) MOLECULE TYPE: DNA primer ( i x ) FEATURE:
( A ) NAME/KEY: N=INOSINE
( B ) LOCATION: 12

( i x ) FEATURE:
( A ) NAME/KEY: N=INOSINE
( B ) LOCATION: 15

( x i ) SEQUENCE DESCRIPTION: SEQ ID NO:14:

ACWCATGAAA TNGSNCAT                                                                                              18

( 2 ) INFORMATION FOR SEQ ID NO:15:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( i i ) MOLECULE TYPE: DNA primer ( x i ) SEQUENCE DESCRIPTION: SEQ ID NO:15:

```
AATACGACTC ACTATAG                                                                    17
```

(2) INFORMATION FOR SEQ ID NO:16:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA primer (xi) SEQUENCE DESCRIPTION: SEQ ID NO:16:

```
TGGTATTATA TCACATGAAA TTGGTCATAC                                                      30
```

(2) INFORMATION FOR SEQ ID NO:17:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA primer (xi) SEQUENCE DESCRIPTION: SEQ ID NO:17:

```
CCCAATTGTG TACTGTTGAA ATTTATCAC                                                       29
```

(2) INFORMATION FOR SEQ ID NO:18:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA primer (xi) SEQUENCE DESCRIPTION: SEQ ID NO:18:

```
CGGGATCCTG TGGWTCATG Y TGGGC                                                          25
```

(2) INFORMATION FOR SEQ ID NO:19:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA primer (ix) FEATURE:
        (A) NAME/KEY: N=INOSINE
        (B) LOCATION: 3

(ix) FEATURE:
        (A) NAME/KEY: N=INOSINE
        (B) LOCATION: 6

(ix) FEATURE:
        (A) NAME/KEY: N=INOSINE
        (B) LOCATION: 15

(xi) SEQUENCE DESCRIPTION: SEQ ID NO:19:

```
TANCCNCCRT TRCANCC Y TC                                                               20
```

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following claims:

What is claimed is:

1. An isolated protein comprising an adult filariid nematode cathepsin L cysteine protease protein.

2. The protein of claim 1, wherein said protein, when administered in an effective manner, elicits an immune response against a filariid cysteine protease.

3. The protein of claim 1, wherein said protein has cysteine protease activity.

4. The protein of claim 1, wherein said filariid nematode is selected from the group consisting of Dirofilaria, Acanthocheilonema, Brugia, Dipetalonema, Loa, Onchocerca, Parafilaria, Setaria, Stephanofilaria and Wuchereria filariid nematodes.

5. The protein of claim 1, wherein said filariid nematode comprises *D. immitis*.

6. The protein of claim 1, wherein said protein comprises amino acid sequence SEQ ID NO:13.

7. The protein of claim 1, wherein said protein is encoded by a nucleic acid sequence comprising SEQ ID NO:12.

8. The protein of claim 1, wherein said protein is produced by a process comprising culturing in an effective medium a recombinant cell transformed with a nucleic acid molecule encoding said protein to produce said protein.

9. The protein of claim 1, wherein said protein is used to identify an inhibitor of cysteine protease activity.

* * * * *